(12) United States Patent
Yamamoto et al.

(10) Patent No.: US 7,141,413 B2
(45) Date of Patent: Nov. 28, 2006

(54) INCUBATOR

(75) Inventors: Hiroshi Yamamoto, Neyagawa (JP); Yasuhiko Yokoi, Hirakata (JP); Mikio Houjou, Higashiosaka (JP); Daisuke Etou, Hirakata (JP); Ayako Michida, Moriguchi (JP); Akihiko Yamada, Hirakata (JP); Akira Sakaguchi, Osaka (JP); Masaki Harada, Yawata (JP); Hiroki Busujima, Ota (JP); Yuichi Tamaoki, Oizumi-Machi (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 61 days.

(21) Appl. No.: 10/715,126

(22) Filed: Nov. 18, 2003

(65) Prior Publication Data

US 2004/0152188 A1    Aug. 5, 2004

(30) Foreign Application Priority Data

Nov. 19, 2002  (JP)  ............................ 2002-334593
Sep. 29, 2003  (JP)  ............................ 2003-338899

(51) Int. Cl.
*C12M 1/36*   (2006.01)

(52) U.S. Cl. .............................. 435/286.2; 435/287.3; 435/288.7; 435/303.1

(58) Field of Classification Search ............. 435/286.2, 435/287.3, 288.7, 303.1
See application file for complete search history.

(56) References Cited

U.S. PATENT DOCUMENTS

| 5,270,173 A | 12/1993 | Yonemori et al. ............ 435/29 |
| 6,673,595 B1 * | 1/2004 | Barbera-Guillem ...... 435/286.2 |

FOREIGN PATENT DOCUMENTS

| JP | 11-89559 | 4/1999 |
| JP | 2002-538477 | 11/2002 |
| JP | 2003-21628 | 1/2003 |
| JP | 2003-093041 | 4/2003 |
| WO | WO 00/53720 | 9/2000 |
| WO | WO 02/064812 A1 | 8/2002 |

* cited by examiner

*Primary Examiner*—David Redding
(74) *Attorney, Agent, or Firm*—Armstrong, Kratz, Quintos, Hanson, & Brooks, LLP.

(57) ABSTRACT

The invention provides an incubator 1 wherein stackers 3 having a plurality of microplate accommodating portions are arranged in a chamber 11, and a microplate transport device 5 is arranged for transporting a microplate 31 within the chamber 11 and moving the microplate 31 into or out of a desired microplate accommodating portion. A camera 7 is provided on a position opposed to a microplate accommodating portion of an uppermost stage in the stacker 3. The camera 7 faces said microplate accommodating portion, whereby a sample on the microplate 31 can be photographed.

2 Claims, 25 Drawing Sheets

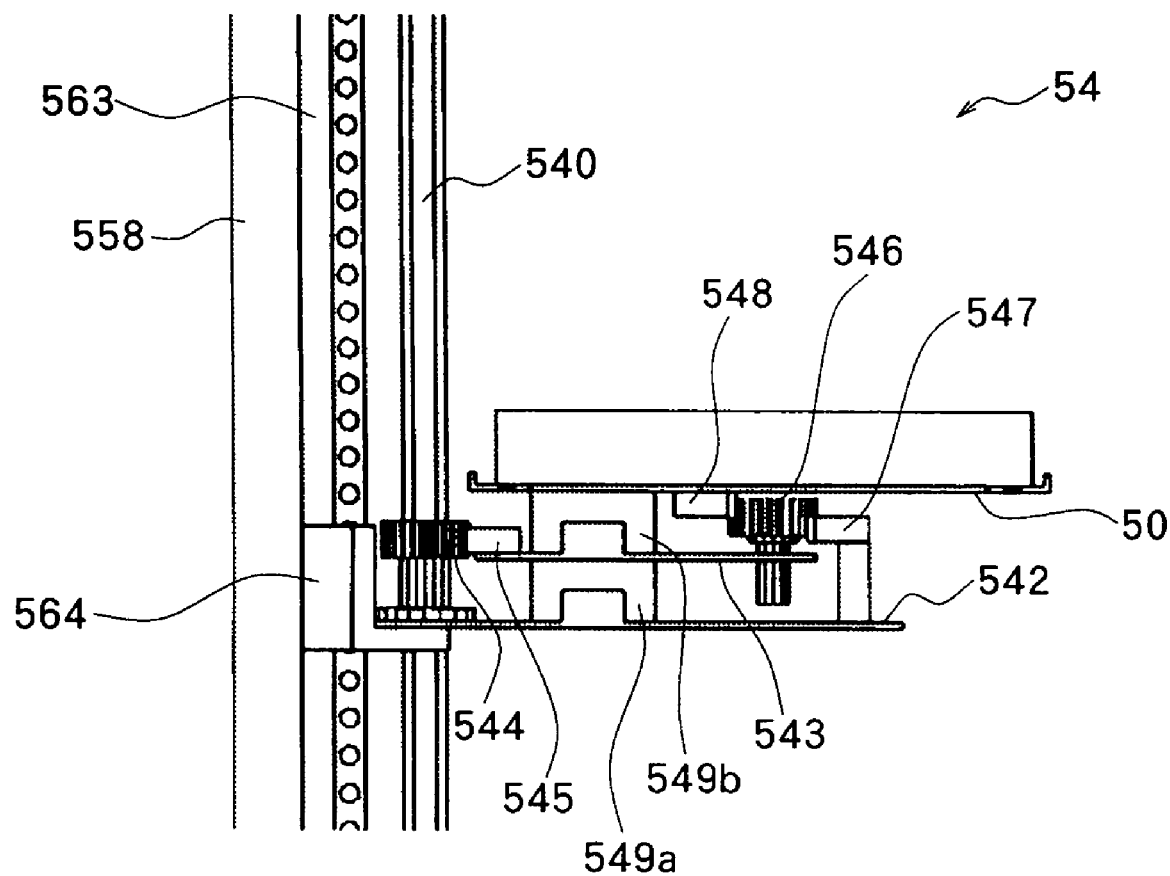

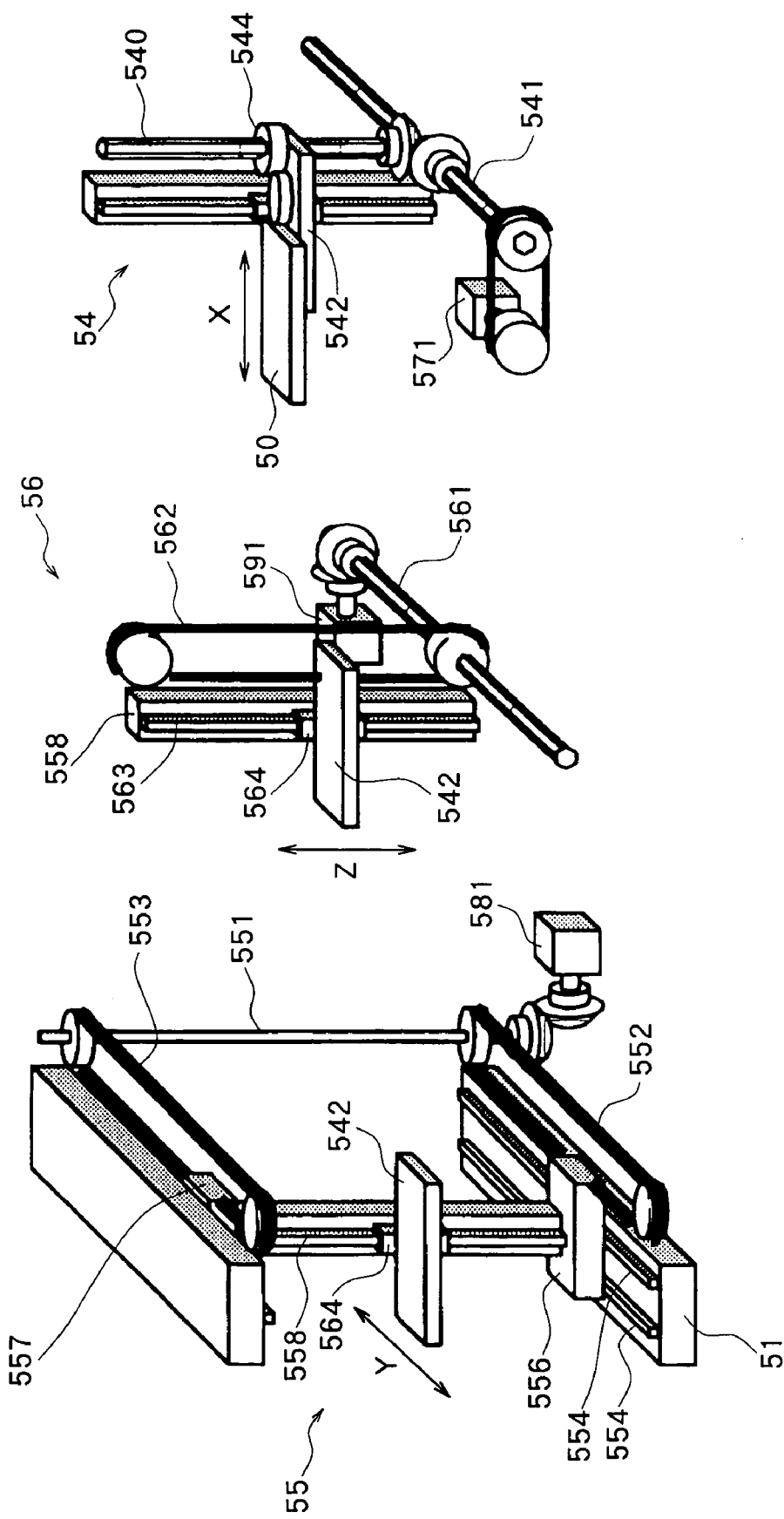

INCUBATOR

FIELD OF THE INVENTION

The present invention relates to incubators for culturing samples on culture containers such as microplates within a chamber which is adjusted to predetermined ambient conditions.

BACKGROUND OF THE INVENTION

FIG. 29 shows an incubator 9 conventionally used for culturing various microorganisms or cells. The incubator 9 comprises a chamber 91 having an opening 90 closable with a door 92 and a plurality of racks 93 arranged in the interior of the chamber, and is adapted to place a plurality of microplates 31 on the respective racks 93. The chamber 91 is provided with an environment adjusting device (not shown) for adjusting the ambient conditions inside the chamber 91, such as temperature, humidity, carbon dioxide concentration, etc. Samples on the microplates 31 are cultured under suitable ambient conditions set by the device.

To check the state of samples being cultured in the incubator 9, the microplate 31 is withdrawn from the chamber 91, and the samples are observed or analyzed using, for example, a microscope. Since the door 92 of the chamber 91 must be opened at such a time, there is the problem that the interior ambient conditions of the chamber 91 are greatly altered by opening the chamber.

Accordingly, an incubator has been proposed in which the microplate is made transportable between a microplate inlet formed in the chamber and a microplate accommodating portion within the chamber so that the microplate can be moved into or out of the accommodating portion automatically (see, for example, the publication of JP-A No. 1999-89559). Because the proposed incubator can be thus adapted by forming a small microplate inlet in the chamber, the internal ambient conditions of the chamber will not be altered greatly by moving the microplate into or out of the chamber.

Furthermore an incubator has been proposed which comprises a microscopic observation device having a camera and an optical system and arranged inside the chamber, and which is adapted to observe the microplates in the chamber with use of the microscopic observation device (see, for example, the publication of JP-T No. 2002-538477, JP-A No. 2003-93041, JP-A No. 2003-21628). The incubator makes it possible to observe the microplates in the chamber without opening the door of the chamber, so that interior ambient conditions of the chamber 91 are not altered.

However, with the conventional incubator which is adapted to automatically transport the microplates in the chamber, for the observation of the sample being cultured, the microplate into which the sample is injected needs to be delivered from the microplate accommodating rack to the microplate inlet and to be withdrawn from the inlet to the outside. After the observation the microplate must be transported to the interior of the chamber, and be returned to the original microplate accommodating portion. Accordingly there arises the problem that the observation of the sample takes much time, and the internal ambient conditions of the chamber are altered because the inlet is opened every time the microplate is moved into or out of the chamber.

On the other hand, with the incubator having arranged inside the chamber the microscopic observation device of the microplate, while internal ambient conditions of the chamber are not altered, there is the problem that high internal humidity of the chamber causes damage to the camera and optical system such as lenses constituting the microscopic observation device.

SUMMARY OF THE INVENTION

A first object of the present invention is to provide an incubator which is adapted to automatically transport a culture container within a chamber, the incubator wherein the observation and analysis of a sample does not take much time and the ambient conditions inside the chamber are not altered.

The present invention provides an incubator which comprises a chamber 11, a culture container accommodating rack having a plurality of culture container accommodating portions and disposed inside the chamber 11, and a culture container transport device for moving the culture container into or out of a desired culture container accommodating portion within the chamber 11. A camera 7 is attached in the chamber 11, and the camera facing a specified position wherein the culture container is to be photographed. By transporting the culture container to the specified position, the sample on the culture container is photographable.

With the incubator of the present invention, for the observation of the sample on the culture container accommodated in the culture container accommodating rack, the culture container transport device moves the culture container out of the accommodating rack to the specified position. This makes it possible to photograph the sample on the container using the camera 7 with the container set at a photographing area of the camera 7. After photographing, the container is delivered from the specified position to the original accommodating portion by the transport device, to thereby accommodate the container to the original accommodating portion.

Stated specifically, the specified position is provided on a particular accommodating portion of the accommodating rack. According to the specific construction, the container to be photographed is taken out of the accommodating rack by the transport device, and is thereafter delivered to the particular accommodating portion to accommodate the container into the portion. Consequently the container is set at a photographing area of the camera 7, making it possible to photograph the sample on the container with the camera 7.

Stated specifically, the camera 7 is attached to an output end of a camera drive mechanism 71, and is driven into the directions of two axes along a surface of the container. The optical axis of the camera 7 is successively positioned on the sample cavities arranged on the surface of the container, to photograph the sample injected into each of the cavities.

Stated further specifically, a signal output end of the camera 7 is connected to display means, and an image photographed by the camera 7 is shown on the display means. This makes it possible to observe the sample in the chamber 11 from the outside of the chamber 11.

According to another specific construction, a signal output end of the camera 7 is connected to an analyzer 72 for performing a predetermined image processing and calculation processing for an image signal obtained from the camera 7 to analyze the sample on the container. This brings an analysis result describing the growth of the sample on the container.

As described above, with the incubator of the present invention, for the observation and the analysis of the sample, delivering the container into which the sample is injected within the chamber is only required while taking the container out of the chamber to the outside is not required, so that the time required is not only shortened, but the ambient conditions in the chamber are held constant.

A second object of the present invention is to provide an incubator which comprises a chamber and a microscopic observation device of the culture container arranged inside the chamber, the incubator wherein the moisture will not cause damage to a camera and an optical system of a lens constituting a microscopic observation device.

The incubator of the present invention comprises a microscopic observation unit 8 housed in the chamber 11, the microscopic observation unit 8 having a microscopic observation device 8a housed in a shield case 80 with a closed construction, the shield case 80 having an observation window 88 disposed on a position opposed to a culture container accommodated in the chamber 11, the culture container being microscopic observable through the observation window 88 by the microscopic observation device 8a.

With the incubator of the present invention, by the provision of the container to be observed on a position opposed to the observation window 88 of the microscopic observation unit 8, the culture container can be observed with the observation device 8a. The microscopic observation device 8a is disposed inside the shield case 80. The interior of the shield case 80 is shut out from the highly humid atmosphere of space wherein the container is accommodated, thereby rendering the observation device 8a free of the influence of moisture.

Stated specifically, the microscopic observation unit 8 comprises a drive device 8b for moving the microscopic observation device 8a. The drive device 8b and the microscopic observation device 8a are housed in the shield case 80. According to the specific construction, fine dusts produced by the drive device 8b will not exert an adverse effect on the container because the drive device 8b is housed in the shield case 80.

Stated further specifically, a culture container transport device for transporting the culture container and stacker holders 23 for arranging thereon stackers 3 having a plurality of culture container accommodating racks are arranged inside the chamber. The microscopic observation unit 8 has a contour wherein the observation unit 8 can be disposed on the stacker holder 23 in place of the one or a plurality of stackers 8. By the replacement of the one or a plurality of stackers on the stacker holder 23 by the microscopic observation unit 8, the microscopic observation unit 8 is set inside the chamber 11, thereby allowing the microscopic observation of the container with the microscopic observation unit 8. At this time the container can be delivered to the position opposed to the observation window 88 of the microscopic observation unit 8 by the operation of the transport device.

As described above, with the incubator of the present invention, the microscopic observation device is housed in the shield case, whereby there is no likelihood that the moisture causes damage to the camera and the optical system of lens constituting the microscopic observation device.

BRIEF DESCRIPTION OF THE DRAWINGS

FIG. 9 is a side elevation of an X-axis transport assembly;

FIG. 11(*a*), FIG. 11(*b*) and FIG. 11(*c*) are perspective views showing power transmission paths of a Y-axis transport assembly, Z-axis transport assembly and the X-axis transport assembly;

DETAILED DESCRIPTION OF EMBODIMENT

An example of the present invention will be described below with reference to the drawings.

Overall Construction

Figure 1:
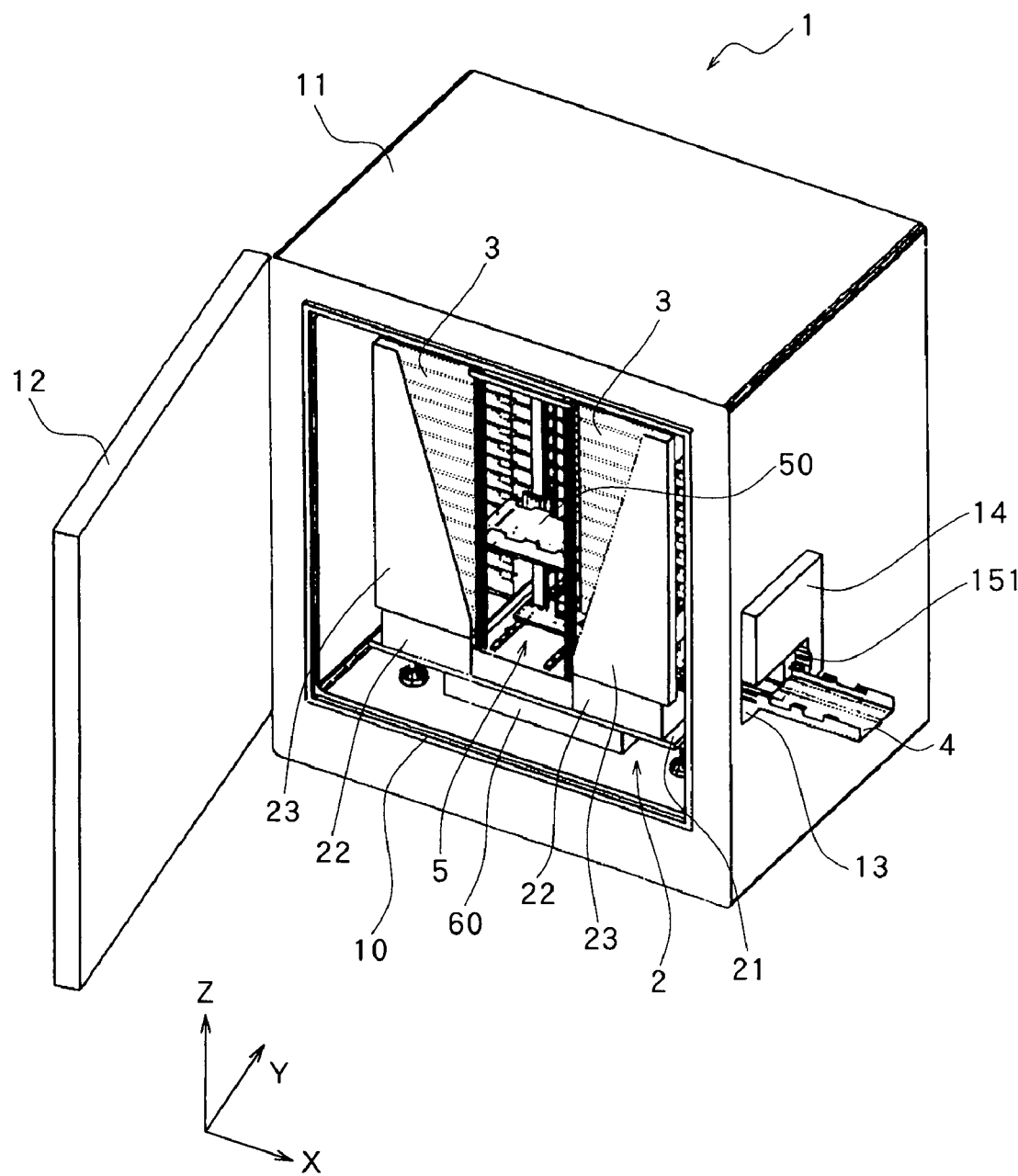
FIG. 1 is a perspective view showing the appearance of an incubator embodying the invention.
Figure 2:
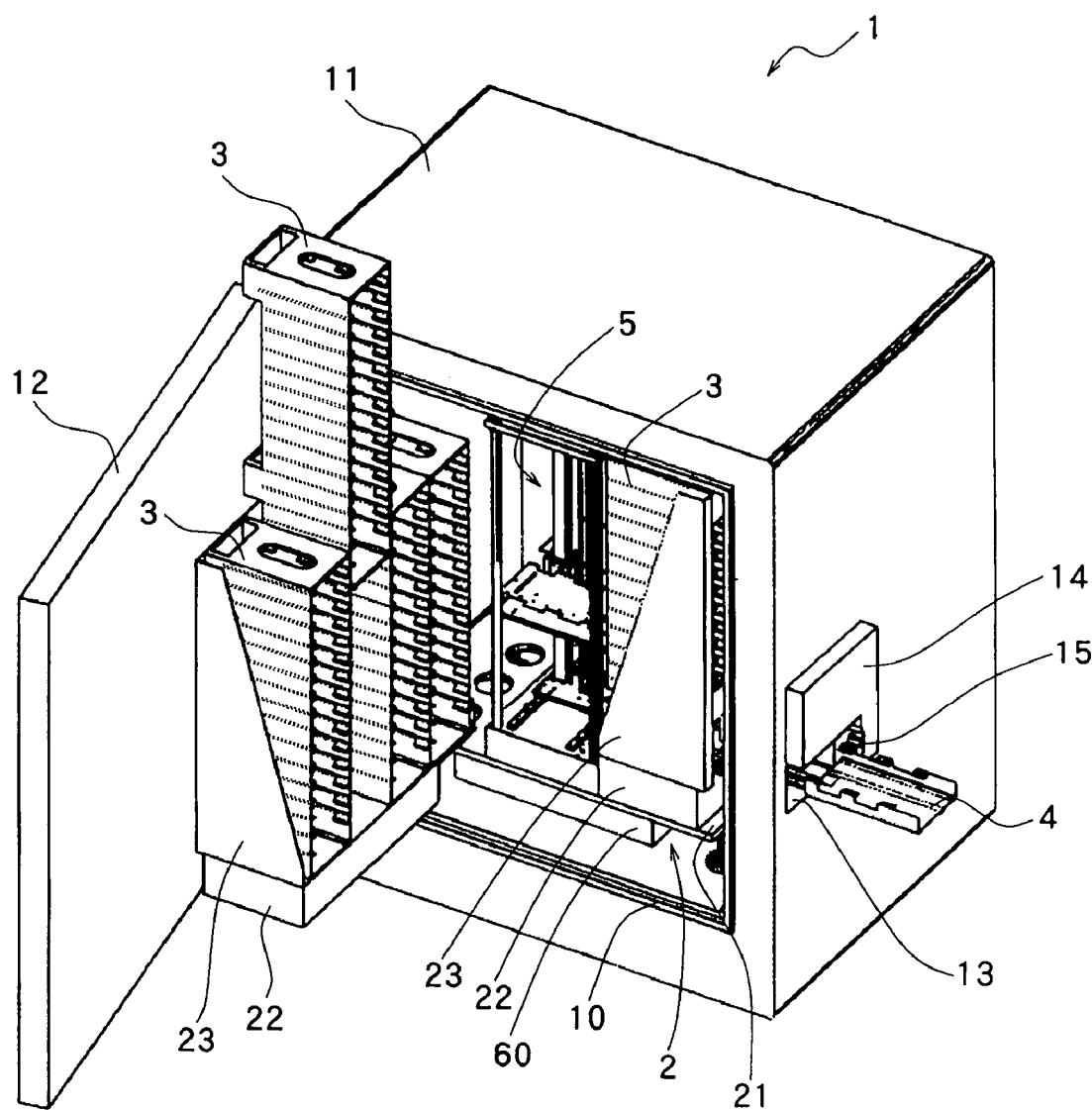
FIG. 2 is a perspective view showing stackers as withdrawn from a chamber.

With reference to FIGS. 1 and 2, an incubator 1 embodying the present invention comprises a chamber 11 having a front opening 10 and a door 12 for closing the opening 10. An incubator unit 2 is accommodated in the interior of the chamber 11. A microplate inlet 13 is formed in a side wall of the chamber 11 and has a microplate carriage mechanism 4 attached thereto.

Figure 3:
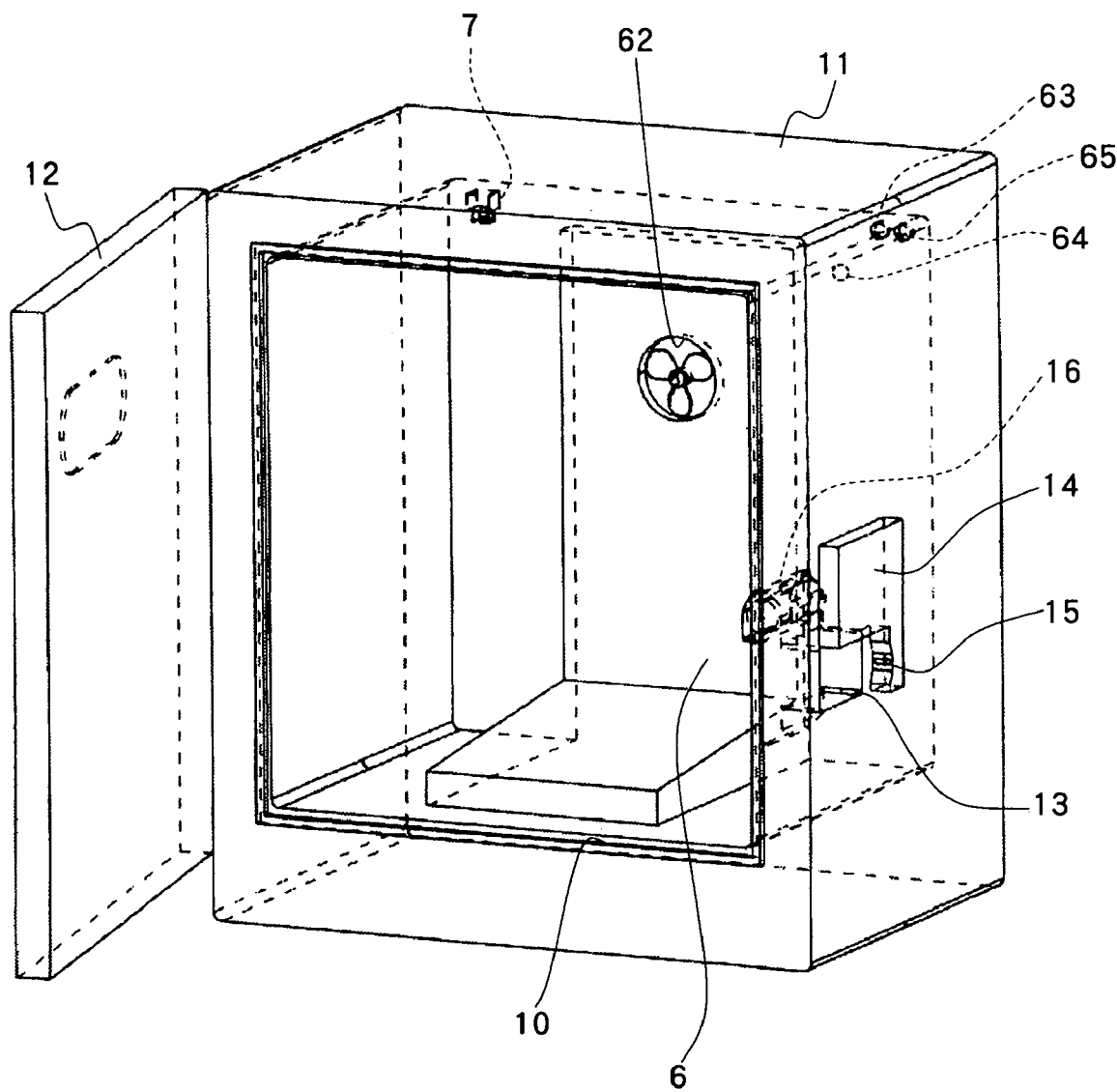
FIG. 3 is a perspective view of the chamber.

As shown in FIG. 3, the chamber 11 has in an inner portion thereof an environment adjusting device 6 for adjusting the temperature, humidity and the concentration of $CO_2$ inside the chamber. The innermost wall of the chamber 11 has a discharge outlet 62 provided with a fan for forcing out a gas for adjusting the environment as specified by the device 6 toward the space in the center of the chamber. Attached to the inside wall of the chamber 11 are a thermometer 63, $CO_2$ densitometer 64 and hygrometer 65 which constitute a sensor unit of the environment adjusting device 6. A camera 7 is installed on the ceiling wall of the chamber 11.

A side wall of the chamber 11 is provided with a shutter mechanism 14 for closing the inlet 13 and an air curtain mechanism 16 for producing an air flow curtain for the inlet 13. The chamber 11 is further provided with a bar code sensor 151 facing the inlet 13 for reading a bar code provided on a microplate during passage through the inlet 13.

Figure 4:
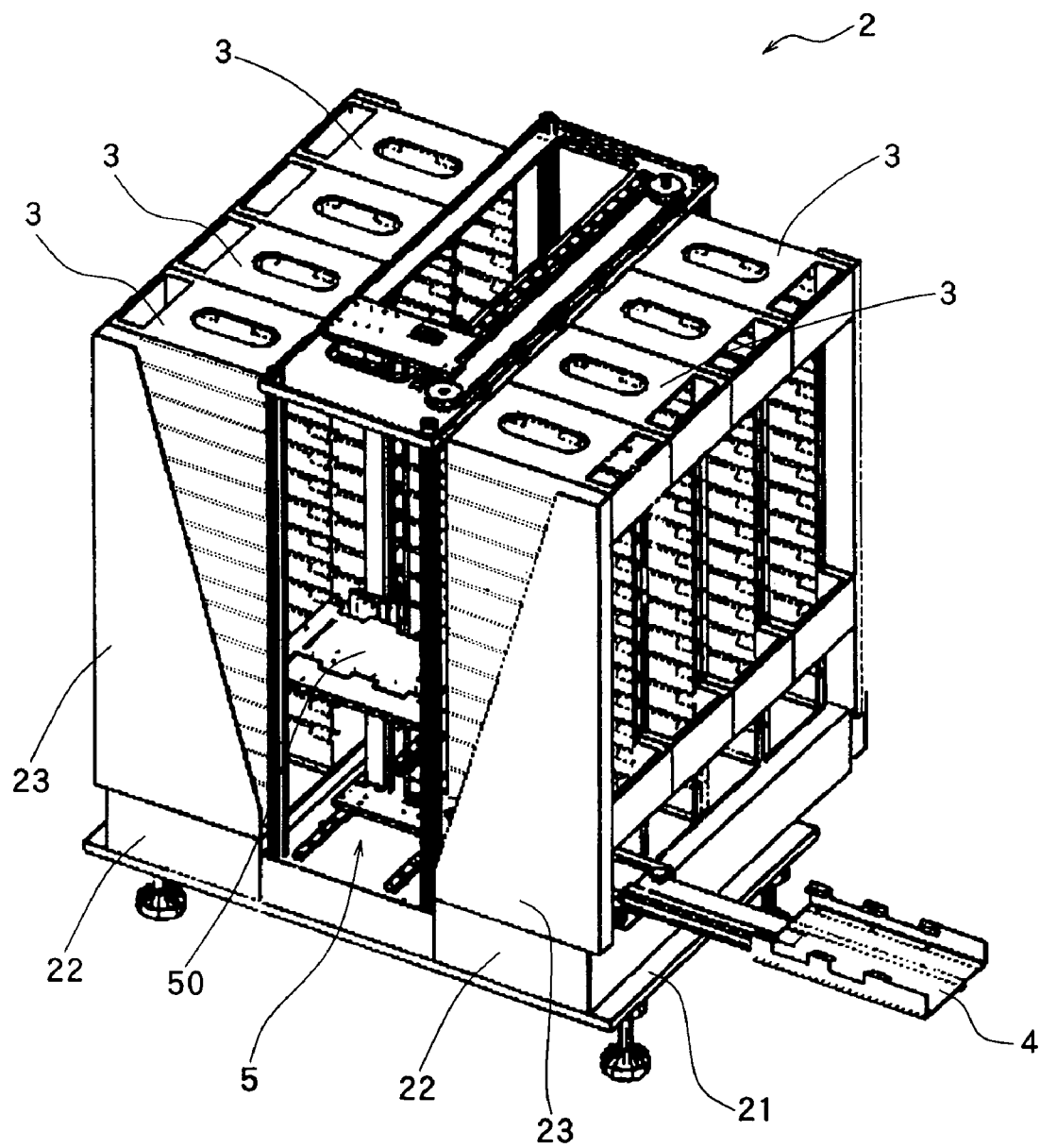
FIG. 4 is a perspective view of an incubator unit.

With reference to FIG. 4, the incubator unit 2 comprises, as mounted on a base 21, a microplate transport device 5 having a microplate transport table 50, and a pair of left and right stacker holders 23, 23 arranged on opposite sides of the transport device 5. The stacker holder 23 retains thereon a plurality of stackers 3 arranged forward or rearward for accommodating microplates.

The stackers 3 on a drawer 22 can be brought out of the opening 10 by withdrawing the drawer 22 through the opening 10 with the door 12 opened as seen in FIG. 2, and the stackers 3 can be withdrawn from the holder 23. The stacker 3 can then be readily replaced by another one and the stacker 3 can be cleaned after use.

Figure 5A:
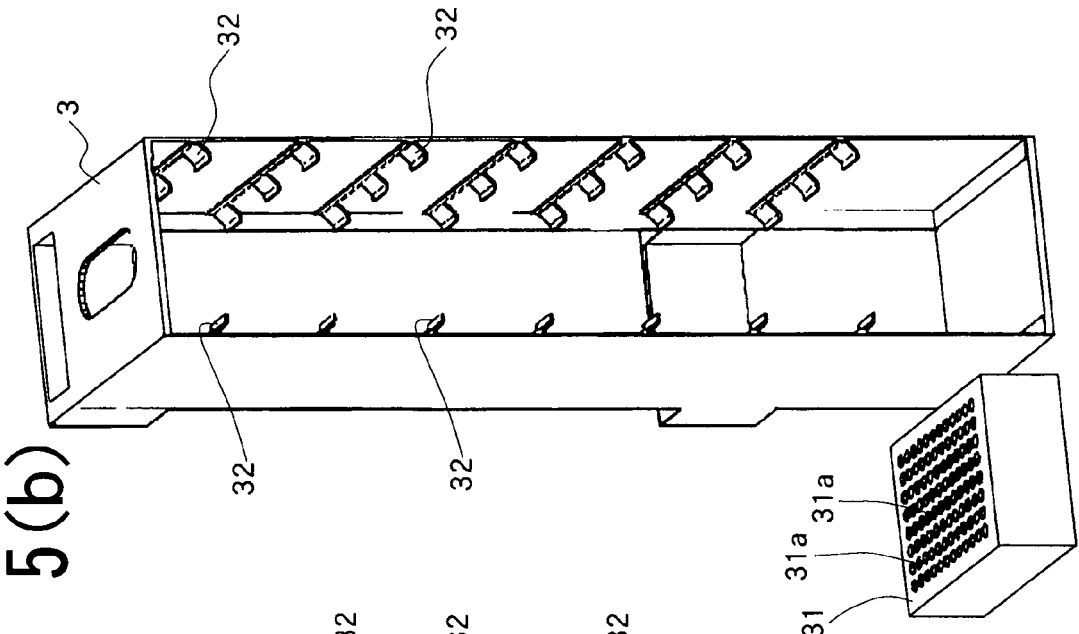
FIG. 5(*a*) and FIG. 5(*b*) are perspective views showing two kinds of microplates which are different in height and two kinds of stackers which are different in the number of stages.
Figure 5B:
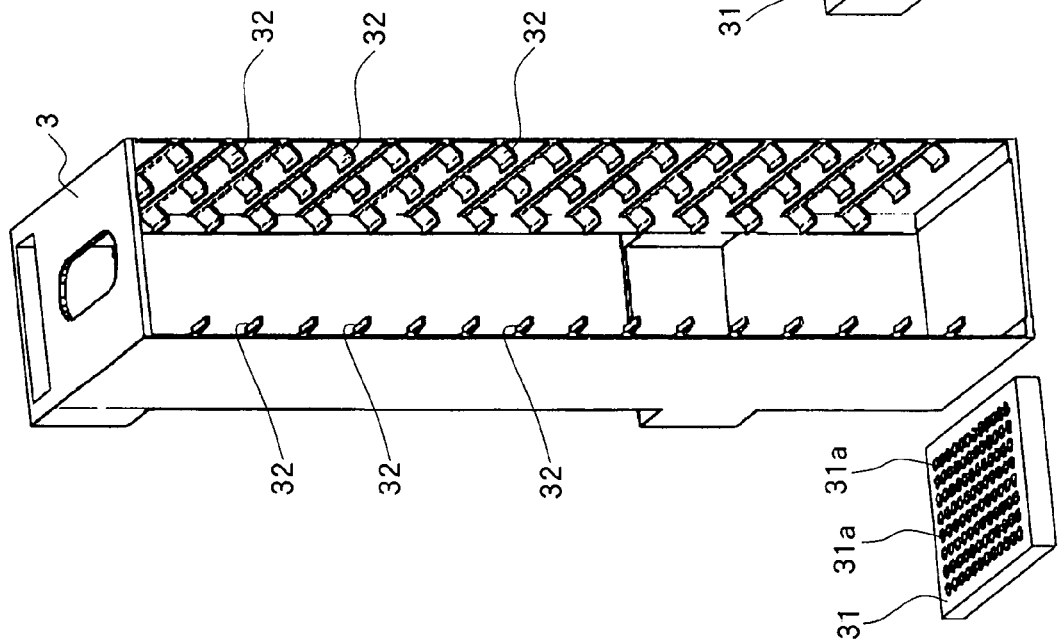

With reference to FIG. 5(*a*) and FIG. 5(*b*), a plurality of microplates 31 each having a plurality of cavities 31*a* for injecting a sample thereinto are accommodated in the stacker 3 in stages. Each of the stages is provided with a pair of support pieces 32, 32 for retaining the microplate 31 in a horizontal posture. Since different kinds of microplates 31 are available which are different in height as illustrated, different kinds of stackers 3 are prepared which are different in the pitch of support pieces 32.

As shown in FIG. 1, the microplate transport device 5 is positioned in the center of the space inside the chamber 11, with the incubator unit 2 accommodated in the chamber 11. Stackers 3 are arranged in the space at each of opposite sides of the device 5. A reservoir pan 60 is disposed below the incubator unit 2 for giving moisture to the air inside the chamber 11.

In the incubator 1 of the present invention, the stackers 3 are arranged within the chamber 1 symmetrically about the transport device 5 on opposite sides thereof as seen in FIG. 1, so that a larger number of stackers 3 can be installed inside the chamber 11 than in the conventional incubator wherein the microplate accommodating racks are provided at only one side of the microplate transport device. An increased number of microplates 31 can therefore be accommodated in the chamber.

Microplate Transport Device 5

Figure 6:
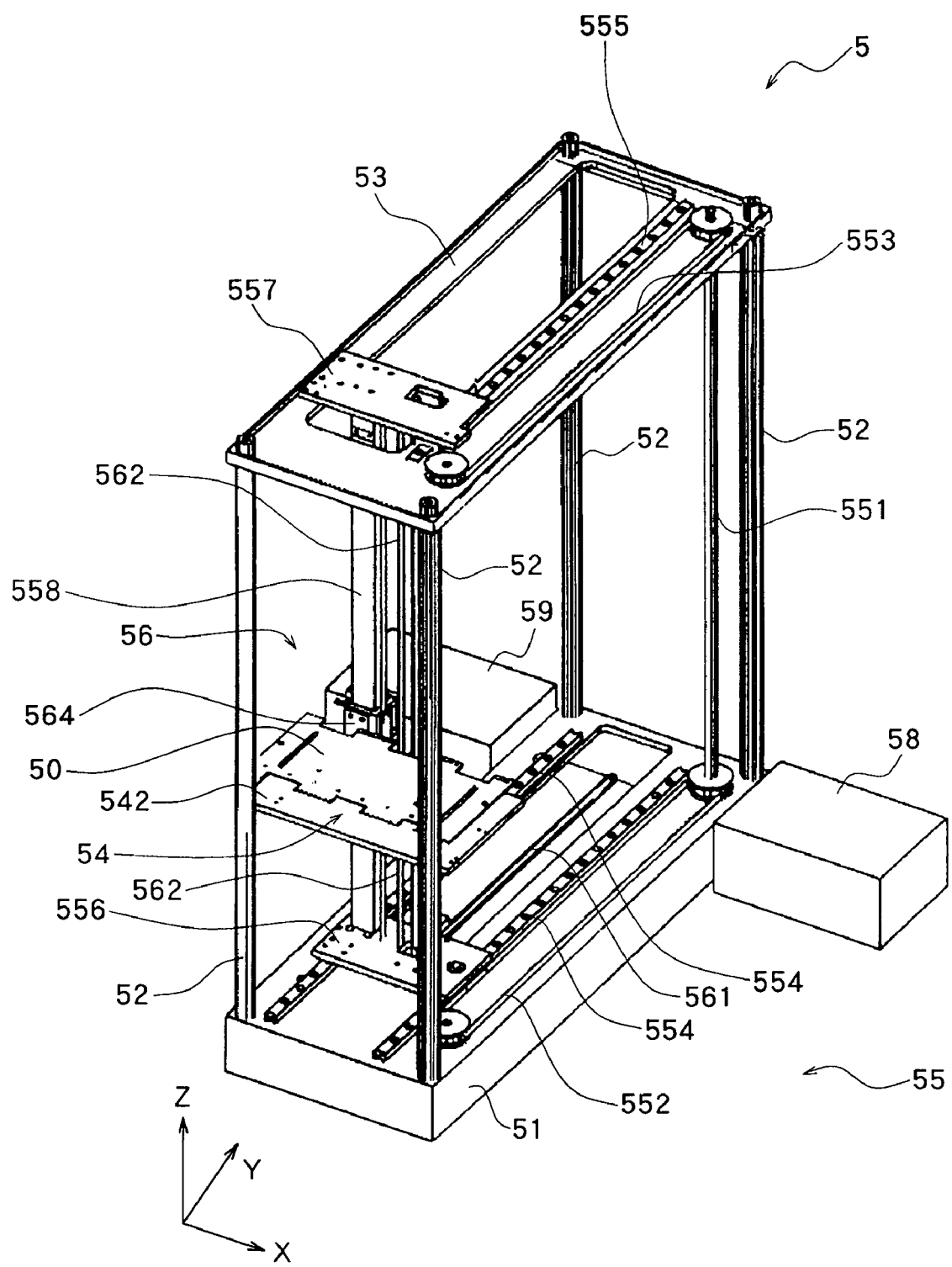
FIG. 6 is a perspective view of a microplate transport device.
Figure 7:
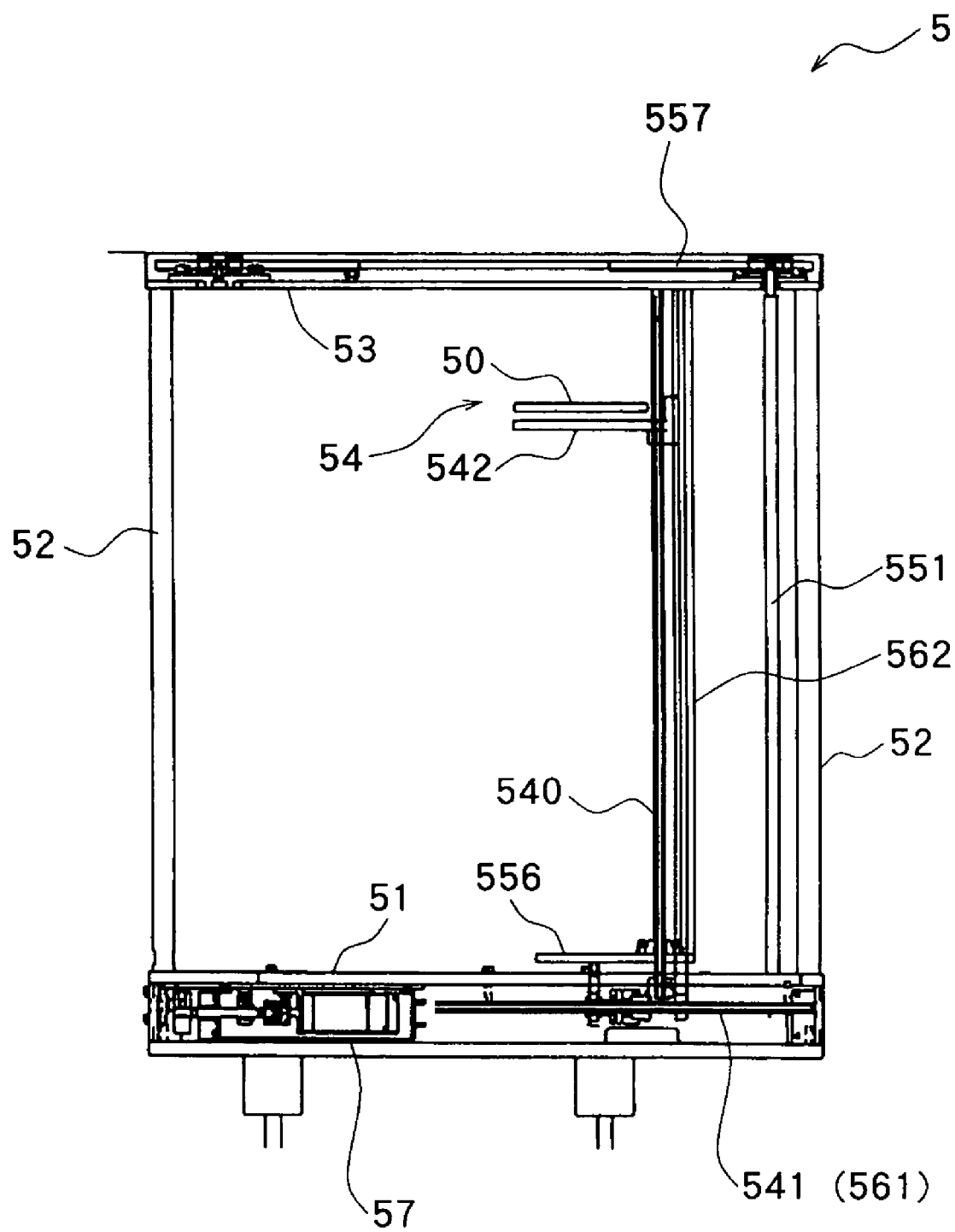
FIG. 7 is a side elevation of the microplate transport device.

The microplate transport device 5 has a frame comprising four posts 52 on a base 51, and an upper plate 53 supported by the posts as shown in FIGS. 6 and 7. The frame is provided with an X-axis transport assembly 54 for driving the transport table 50 in a lateral direction, i.e., in the direction of X-axis, a Y-axis transport assembly 55 for driving the transport table 50 forward or rearward, i.e., in the direction of Y-axis, and a Z-axis transport assembly 56 for driving the transport table 50 upward or downward, i.e., in the direction of Z-axis.

Figure 8:
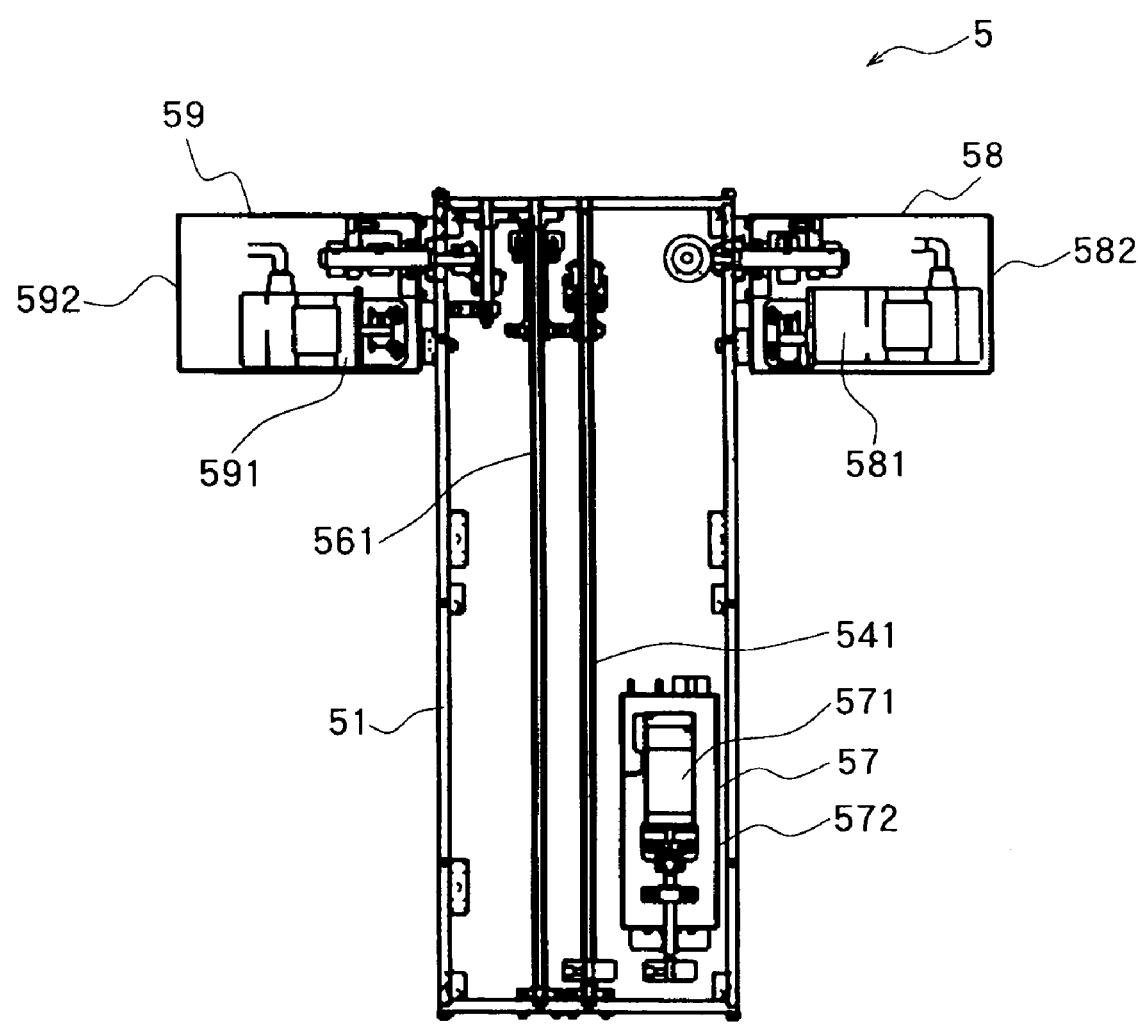
FIG. 8 is a plan view showing the locations of three motors provided for the transport device.

With reference to FIG. 8, mounted on the base 51 are an X-axis motor unit 57 for driving the X-axis transport assembly 54, a Y-axis motor unit 58 for driving the Y-axis transport assembly 55 and a Z-axis motor unit 59 for driving the Z-axis transport assembly 56. The X-axis motor unit 57 comprises an X-axis motor 571 housed in a motor case 572. The Y-axis motor unit 58 comprises a Y-axis motor 581 housed in a motor case 582. The Z-axis motor unit 59 comprises a Z-axis motor 591 housed in a motor case 592. These motors 571, 581, 591 are each a stepping motor.

Y-axis Transport Assembly 55

With reference to FIG. 6, two lower guide rails 554, 554 extending in the direction of Y-axis are installed on the base 51. A lower slide plate 556 is slidably in engagement with the lower guide rails 554, 554. A single upper guide rail 555 extending in the direction of Y-axis is installed on the upper plate 53, and an upper slide plate 557 is slidably in engagement with the rail 555. The lower slide plate 556 and the upper slide plate 557 are interconnected by a vertical bar 558 to provide a reciprocating movable body which is reciprocatingly movable along the direction of Y-axis.

Positioned on the base 51 is a Y-axis drive ladder chain 552 made of stainless steel and extending along the lower guide rail 554. Disposed on the upper plate 53 is a Y-axis drive ladder chain 553 made of stainless steel and extending along the upper guide rail 555. The lower slide plate 556 is connected to one end of the lower ladder chain 552. The upper slide plate 557 is connected to one end of the upper ladder chain 553. Supported by the base 51 and the upper plate 53 is a Y-axis drive shaft 551 extending vertically and to be driven by the Y-axis motor unit 58. The Y-axis drive ladder chains 552, 553 are driven by the rotation of the shaft 551.

Consequently, the lower and upper slide plates 556, 557 are reciprocatingly moved in the directions of Y-axis along the lower guide rails 554, 554 and the upper guide rail 555, and the vertical bar 558 reciprocatingly moves along the direction of Y-axis with this movement.

As shown in FIG. 9, the vertical bar 558 is provided with a guide rail 563 extending in the direction of Z-axis and having a Z-axis slider 564 slidably engaged therewith. A lift plate 542 is supported by the slider 564 and has placed thereon the transport table 50.

The Y-axis transport assembly 55 is thus constructed for driving the transport table 50 in the direction of Y-axis. FIG. 11(*a*) shows the power transmission path of the Y-axis transport assembly 55. The rotation of the Y-axis motor 581 is delivered to the ladder chains 552, 553 for reciprocatingly moving the lower slide plate 556 and the upper slide plate 557 along the direction of Y-axis. This movement reciprocatingly moves the lift plate 542 along the direction of Y-axis. As a result, the transport table 50 is reciprocatingly moved along the direction of Y-axis.

The Y-axis transport assembly 55 comprises the reciprocating movable body having the lower and upper slide plates 556, 557 and the vertical bar 558, and these slide plates 556, 557 are guided by the lower guide rails 554, 554 and the upper guide rail 555, so that the transport table 50 can be moved along the Y-axis in a stabilized posture.

Z-axis Transport Assembly 56

With reference to FIG. 8, the base 51 has mounted thereon a Z-axis drive shaft 561 extending along the direction of Y-axis and to be driven by the Z-axis motor unit 59. Further as shown in FIG. 6, extending between the lower slide plate 556 and the upper slide plate 557 is a Z-axis drive ladder chain 562 made of stainless steel. The lift plate 542 is connected to one end of the chain 562. The rotation of the Z-axis drive shaft 561 is delivered to the ladder chain 562.

The Z-axis transport assembly 56 for driving the transport table 50 along the direction of Z-axis is thus constructed. FIG. 11(*b*) shows the power transmission path of the Z-axis transport assembly 56. The Z-axis motor 591 drives the Z-axis drive shaft 561, which in turn drives the ladder chain 562 to reciprocatingly move the lift plate 542 along the direction of Z-axis.

X-axis Transport Assembly 54

With reference to FIG. 9, a lower-stage slider 549*a* reciprocatingly movable along the direction of X-axis is mounted on the lift plate 542 projecting from the Z-axis slider 564. An intermediate slide plate 543 is fixed to the top of the lower-stage slider 549*a*. An upper-stage slider 549*b* reciprocatingly movable along the direction of X-axis is mounted on the intermediate slide plate 543. The transport table 50 is fixed to the top of the upper-stage slider 549*b*.

With reference to FIG. 8, a horizontal X-axis drive shaft 541 extending in the direction of Y-axis is mounted on the base 51. The rotation of the X-axis motor unit 57 is delivered to one end of the shaft 541. Further as shown in FIG. 7, a vertical X-axis drive shaft 540 extending in the direction of Z-axis is supported by and extends between the lower slide plate 556 and the upper slide plate 557. The rotation of the horizontal shaft 541 is delivered to the lower end of the vertical shaft 540.

With reference to FIG. 9, a first pinion 544 is engaged with the vertical X-axis drive shaft 540 nonrotatably relative to thereto and is slidable on the shaft axially thereof, while a first rack 545 is disposed on the intermediate slide plate 543. The first pinion 544 and the first rack 545 are in mesh with each other. A second pinion 546 is provided on the intermediate slide plate 543, while a second rack 547 is mounted on the lift plate 542. The second pinion 546 and the second rack 547 are in mesh with each other.

The X-axis drive assembly 54 is thus constructed for driving the transport table 50 along the direction of X-axis. FIG. 11(*c*) shows the power transmission path of the assembly 54. The rotation of the X-axis motor 571 is delivered to the pinion 544 via the horizontal X-axis drive shaft 541 and the vertical X-axis drive shaft 540 to drive the transport table 50 along the direction of X-axis by the rotation of the pinion 544.

Figure 10A:
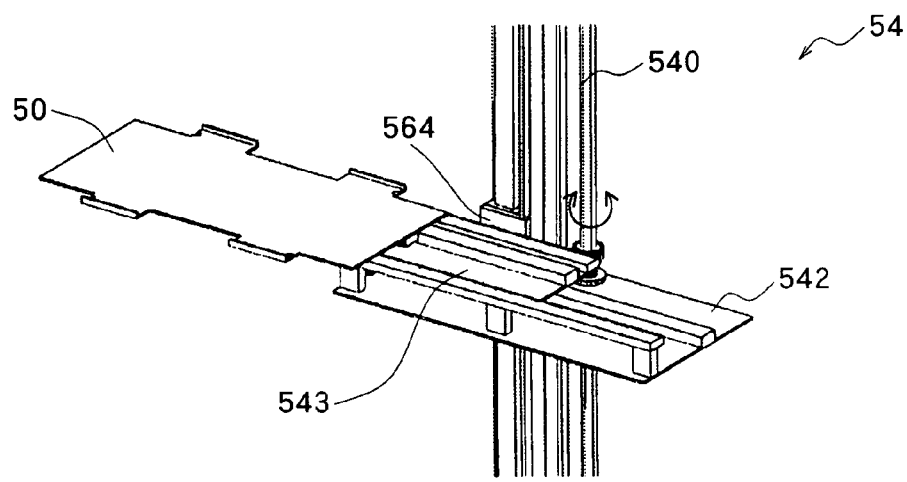
FIG. 10(*a*) and FIG. 10(*b*) are perspective views showing the movement of the X-axis transport assembly.
Figure 10B:
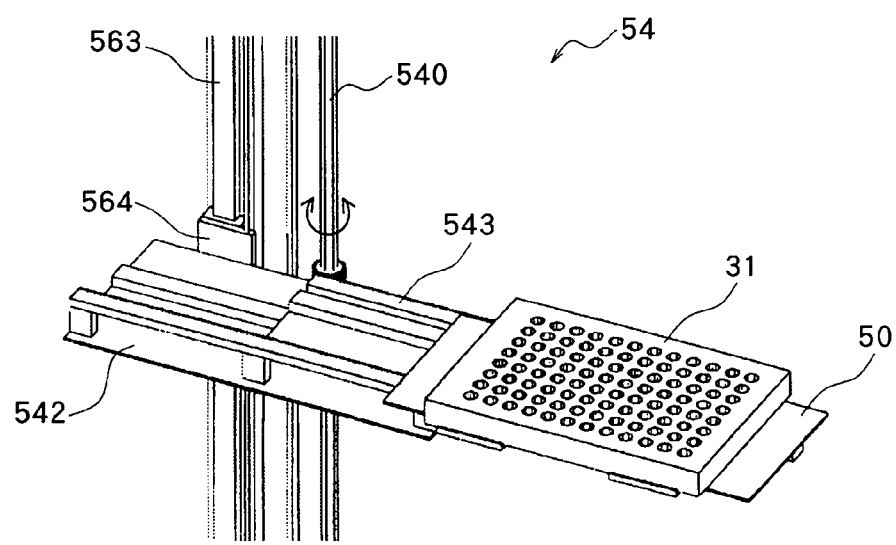

With reference to FIG. 10(*a*) and FIG. 10(*b*) showing the movement of the X-axis transport assembly 54, the transport table 50 in a reference position wherein the table is located in overlapping relation with the lift plate 542 is moved to a leftward limit position shown in FIG. 10(*a*) into the stacker at the left, or to a rightward limit position shown in FIG. 10(*b*) into the stacker at the right, by the forward or reverse rotation of the vertical X-axis drive shaft 540.

Microplate Carriage Mechanism 4

Figure 12:
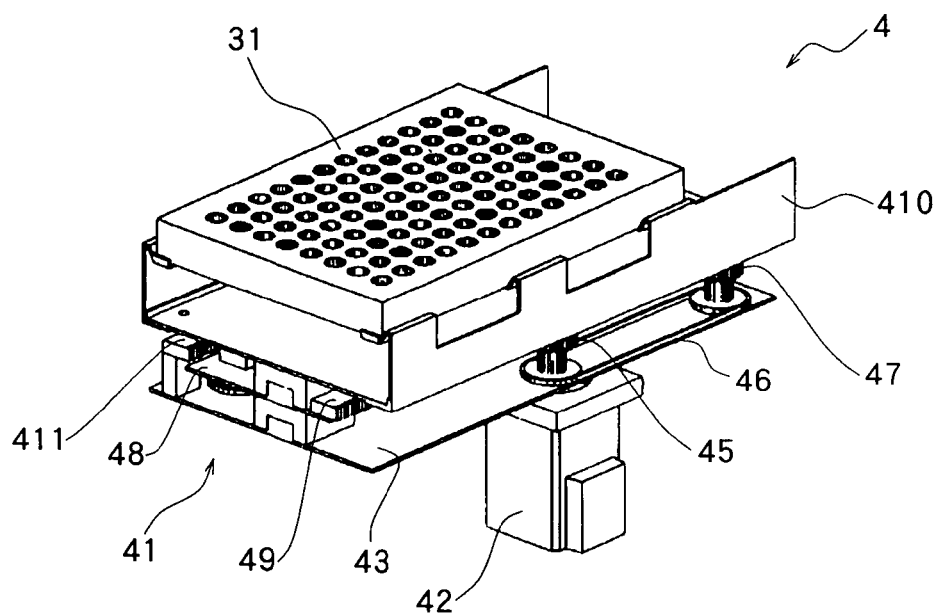
FIG. 12 is a perspective view of a microplate carriage mechanism.
Figure 13:
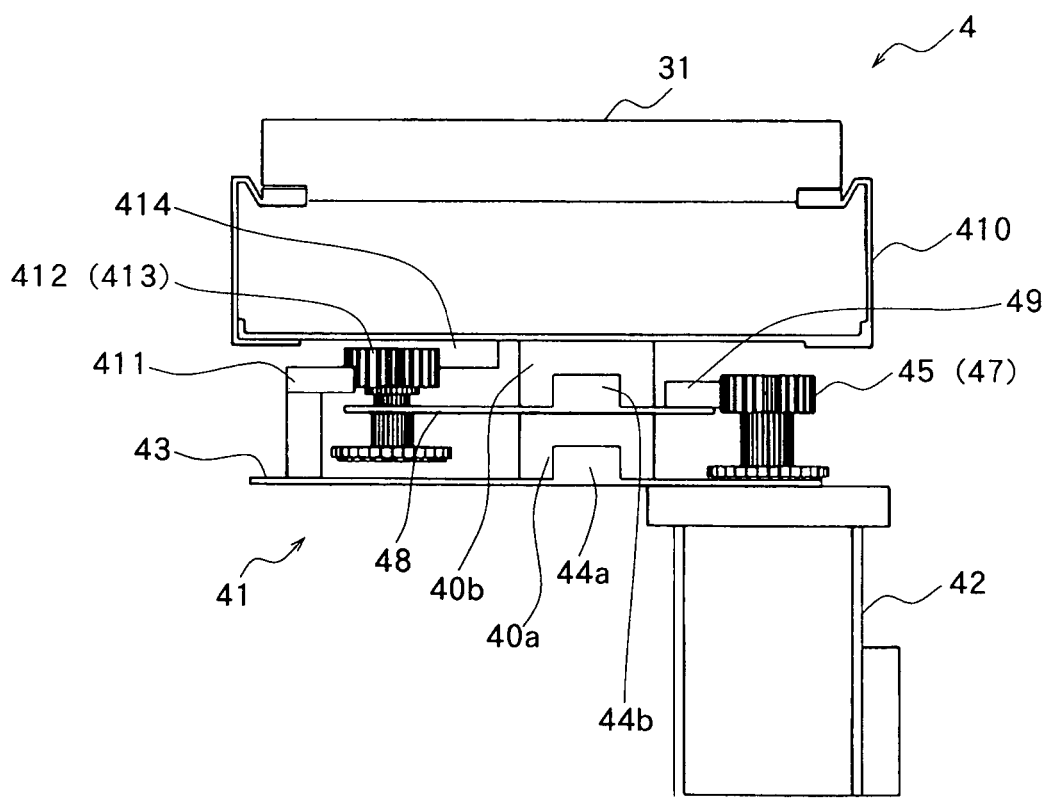
FIG. 13 is a side elevation of the microplate carriage mechanism.
Figure 14:
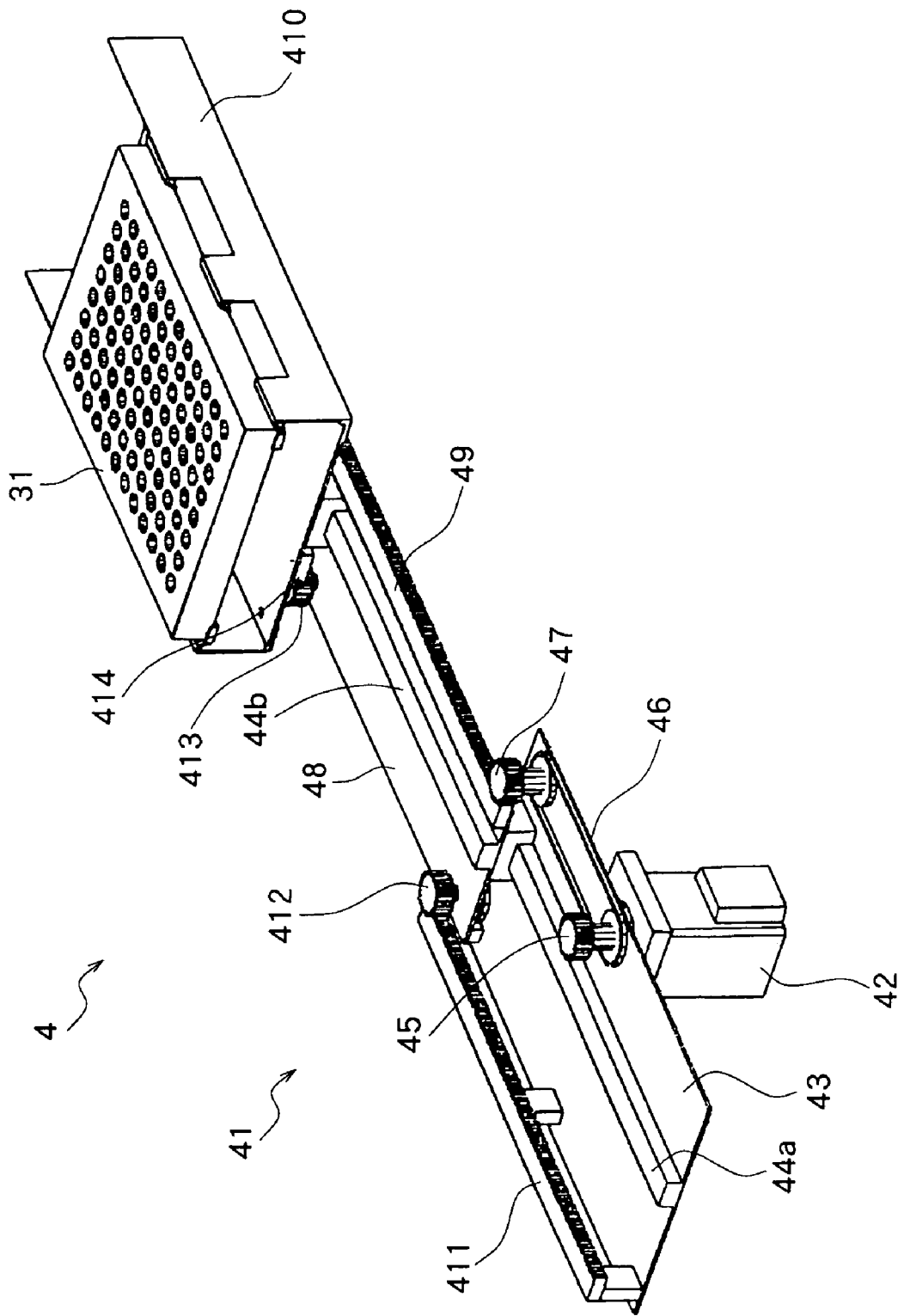
FIG. 14 is a perspective view showing the movement of the microplate carriage mechanism.

With reference to FIGS. 12 to 14, the microplate carriage mechanism 4 comprises a reciprocating transport assembly 41 and a motor unit 42 for driving the assembly 41. The transport assembly 41 has a guide rail 44*a* extending in the direction of X-axis and provided on a base 43, and a lower-stage slider 40*a* is slidably in engagement with the guide rail 44*a*. An intermediate slide plate 48 is fixed to the top of the lower-stage slider 40*a*. A guide rail 44*b* extending in the direction of X-axis is provided on the intermediate slide plate 48, and an upper-stage slider 40*b* is slidably in engagement with the guide rail 44*b*. A microplate carrier 410 is fixed to the top of the upper-stage slider 40*b*.

The base 43 is provided with the carriage motor unit 42, which comprises a stepping motor housed in a motor case. Also mounted on the base 43 are a first and a second pinion 45, 47 to be driven by the motor unit 42 at the same time, while a first rack 49 is mounted on the intermediate slide plate 48. The first pinion 45 and the first rack 49 are opposed to each other in meshing engagement, with the second pinion 47 in mesh with the first rack 49. A third pinion 412 is mounted on the intermediate slide plate 48, while a second rack 411 is mounted on the base 43. The pinion 412 and the rack 411 are in mesh with each other. The slide plate 48 is also provided with a fourth pinion 413, while a third rack 414 is attached to the rear wall of the microplate carrier 410. The pinion 413 and the rack 414 are in mesh with each other.

Accordingly, when the first and second pinions 45, 47 are rotatingly driven clockwise by the carriage motor unit 42 in the state shown in FIG. 12, the intermediate slide plate 48 is driven in the direction of X-axis. At the same time, the microplate carrier 410 on the slide plate 48 is driven along the direction of X-axis, with the result that the carrier 410 is greatly projected from the base 43 as seen in FIG. 14. Alternatively when the first and second pinions 45, 47 are rotatingly driven counterclockwise by the motor unit 42 in the state shown in FIG. 14, the carrier 410 is returned to the initial position shown in FIG. 12.

With the incubator 1 of the present invention, the ladder chains of stainless steel are used in the power transmission mechanisms for the microplate carriage mechanism 4 and the microplate transport device 5 as described above. This obviates the likelihood that the moisture inside the chamber 11 will cause oxidative corrosion to the power transmission mechanisms.

Construction of the Motor Units

As already described, the X-axis motor unit 57, Y-axis motor unit 58, Z-axis motor unit 59 and carriage motor unit 42 each comprise a motor housed in a motor case. Further stated more specifically with reference to FIG. 15 showing the construction of the Y-axis motor unit 58 as an example, the construction is adapted to prevent the condensation of water vapor on the motor.

Figure 15:
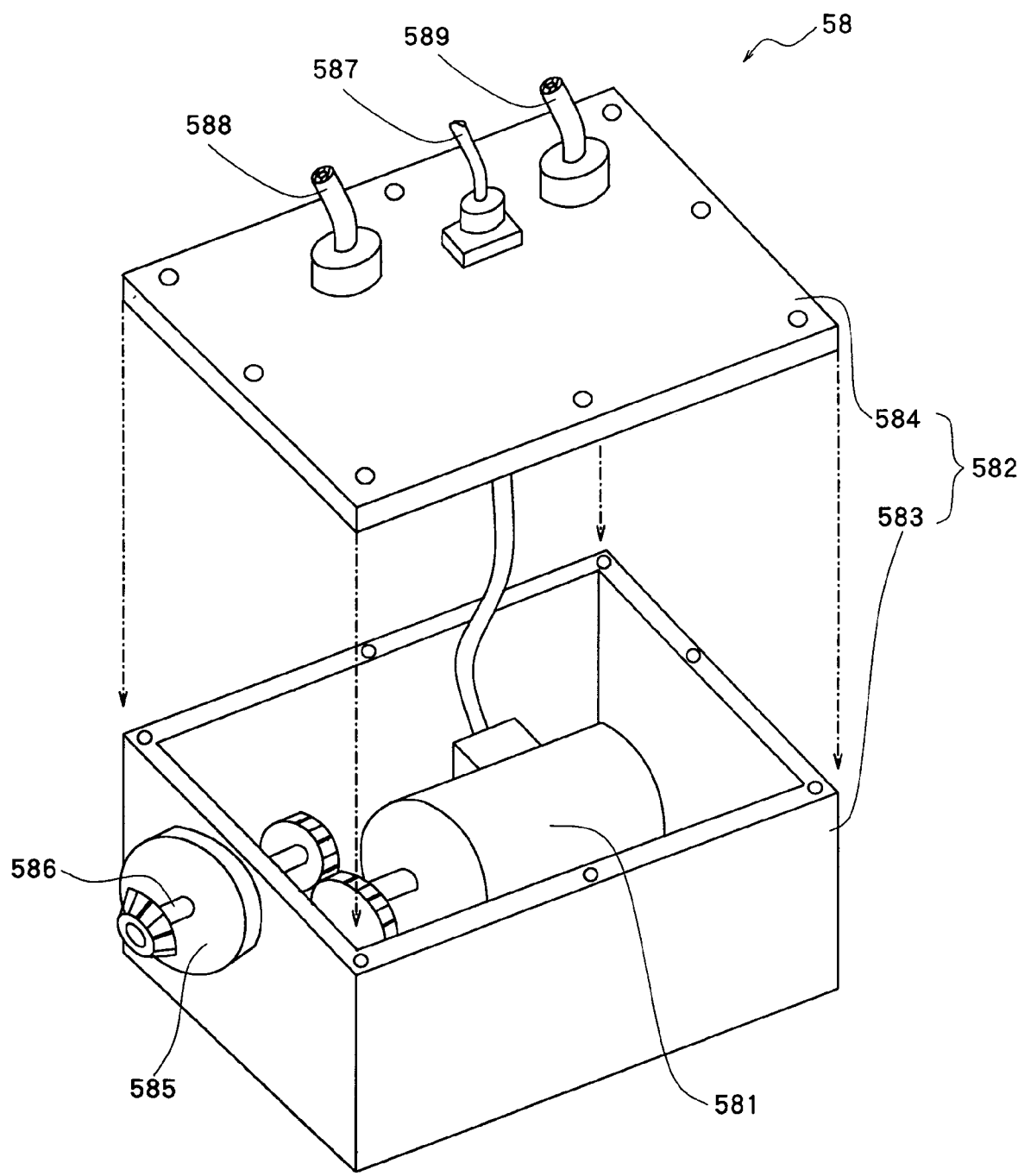
FIG. 15 is an exploded perspective view of a Y-axis motor unit.

In the case of the Y-axis motor unit 58, the motor case 582 comprises a case body 583 and a lid 584 and has its interior hermetically closed, as shown in FIG. 15. The Y-axis motor 581 is housed in the motor case 582 and has an output shaft 586 hermetically extending through a sliding bearing 585 attached to the case 582. The output shaft 586 has an outer end projecting outward from the case 582.

Attached to the lid 584 of the motor case 582 are an air admitting hose 588 for introducing air into the motor case 582 and a vent hose 589 for discharging air from inside the case 582, whereby the air within the motor case 582 is circulated. The lid 584 of the case 582 has also connected thereto a cable 587 for feeding electric power and a control signal to the Y-axis motor 581.

The construction of the motor unit described above holds the interior of the motor case 582 airtight and permits the circulation of air through the motor case 582, so that even if the ambient temperature of the motor unit 50 drops, condensation of water vapor is unlikely to occur inside the case 582. The X-axis motor unit 57, Z-axis motor unit 58 and carriage motor unit 42 also have the same construction as the unit 58 and are made free from the condensation.

Microscopic Observation System

Figure 16:
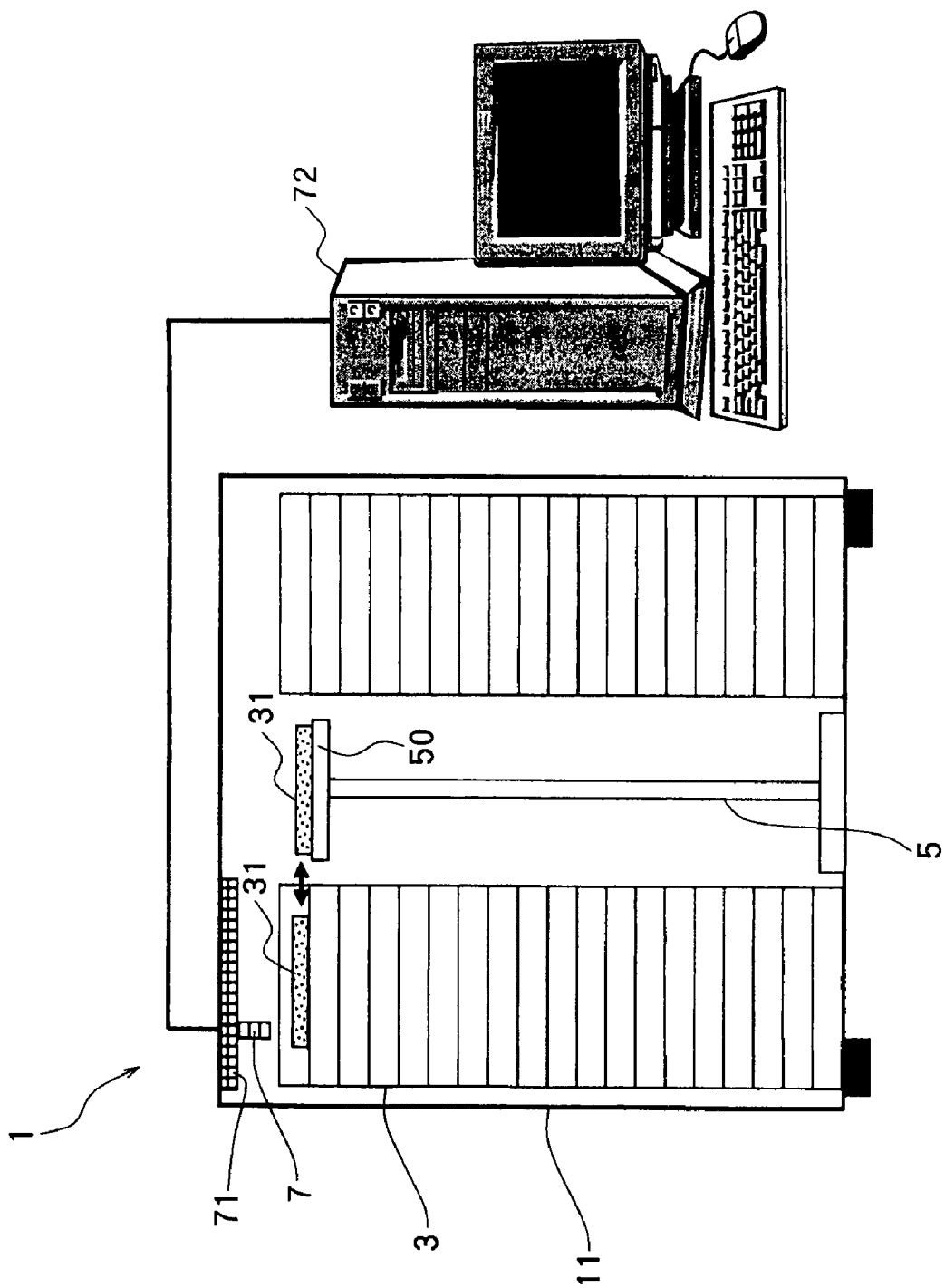
FIG. 16 is a diagram showing a camera provided for the chamber.

The incubator 1 according to the invention further has a camera 7 attached to the ceiling wall of the chamber 11 as seen in FIG. 16. The camera 7 faces the microplate accommodating portion to be photographed and provided at the uppermost stage in the specified stacker 3 for photographing the microplate placed in the accommodating portion. The camera 7 can be driven in the direction of X-axis and the direction of Y-axis by a camera drive mechanism 71. The camera 7 and the drive mechanism 71 are connected to an analyzer 72 for controlling the movement of the camera 7. For the analysis of the sample, the analyzer 72 processes the image data obtained by the camera 7 and performs calculations.

For the camera 7 to photograph the microplate 31, the microplate 31 to be photographed is transported to the microplate accommodating portion to be photographed by the transport device 5. The sample on the microplate 31 is photographed while the camera 7 is being driven along the direction of X-axis and the direction of Y-axis, and the resulting image is fed to the analyzer 72.

Control System

Figure 17:
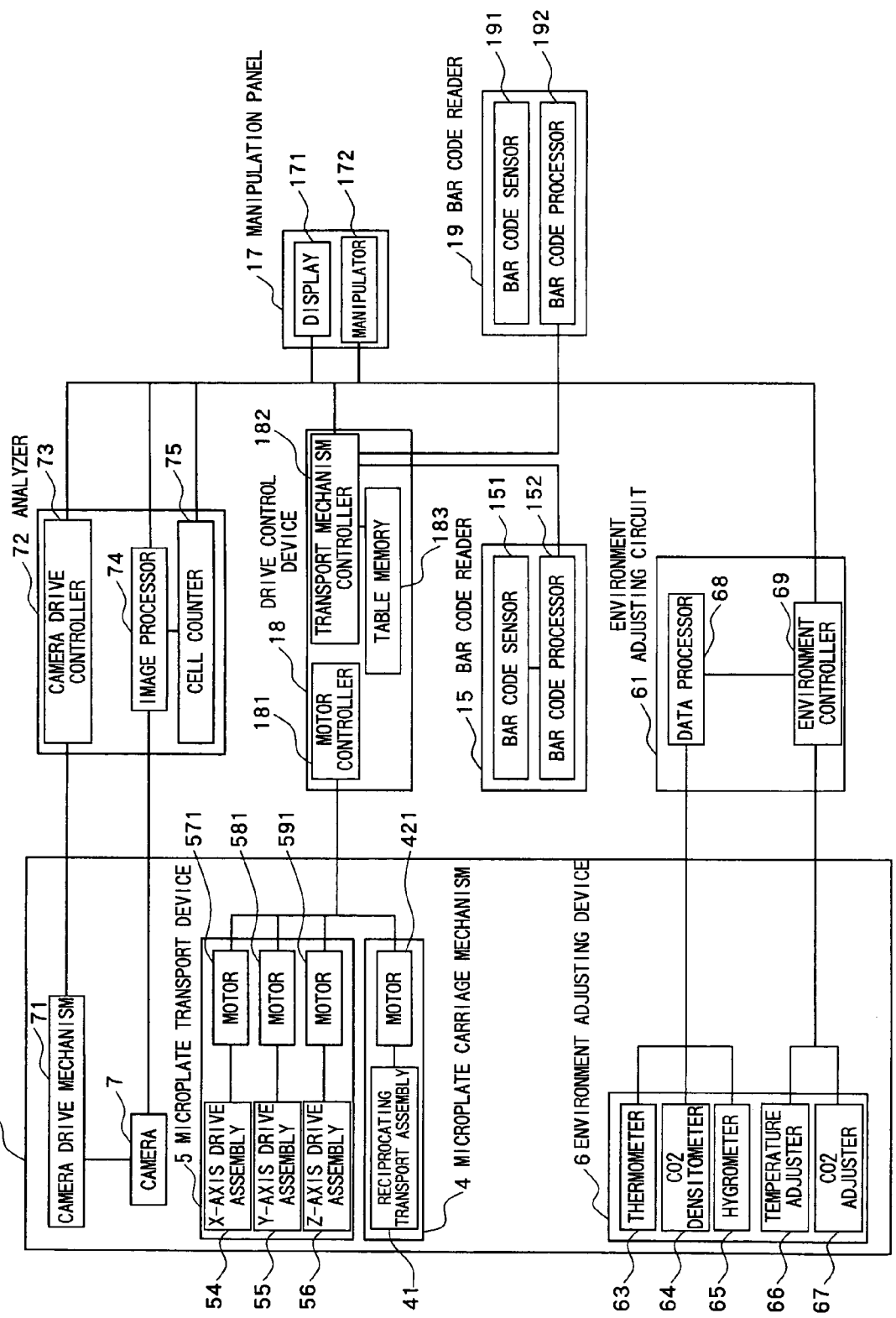
FIG. 17 is a control block diagram of the incubator of the invention.

FIG. 17 shows the construction of a control system of the incubator 1 of the present invention. The microplate carriage mechanism 4 and the microplate transport device 5 are connected to a drive control device 18 comprising a motor controller 181, transport mechanism controller 182 and table memory 183 for controlling the transport of microplates into or out of the chamber 11 and transport of microplates inside the chamber. The environment adjusting device 6 comprises aforementioned thermometer 63, $CO_2$ densitometer 64 and hygrometer 65 which provides a sensor unit, and further comprises a temperature adjuster 66 and $CO_2$ adjuster 67 to be operated according to the detected values obtained by the sensor unit. The device 6 has its operation controlled by an environment adjusting circuit 61 comprising a data processor 68 and an environment controller 69.

The camera 7 and the camera drive mechanism 71 are connected to the analyzer 72, which comprises a camera drive controller 73, image processor 74 and cell counter 75. The camera drive controller 73 controls the drive of the camera 7, and the image data obtained by the camera 7 is processed as required by the image processor 74. The number of cells in the sample on the microplate is counted by the cell counter 75.

A manipulation panel 17 comprising a display 171 and a manipulator 172 is connected to the drive control device 18, environment adjusting circuit 61 and camera drive controller 73. When manipulated, the manipulator 172 gives various operation commands, and the operating state can be monitored by the display 171.

Further connected to the drive control device 18 are a first bar code reader 15 for reading the bar codes provided on microplates 31 and a second bar code reader 19 for reading the bar codes provided on stackers. The first bar code reader 15 is provided by connecting a bar code processor 152 to the bar code sensor 151 which is attached to the microplate inlet 13 as previously stated. The second bar code reader 19 is a unit comprising a bar code sensor 191 and a bar code processor 192, and can be held by the hand to read the bar code on the stacker 3.

Operation of the Incubator (1)

Figure 18:
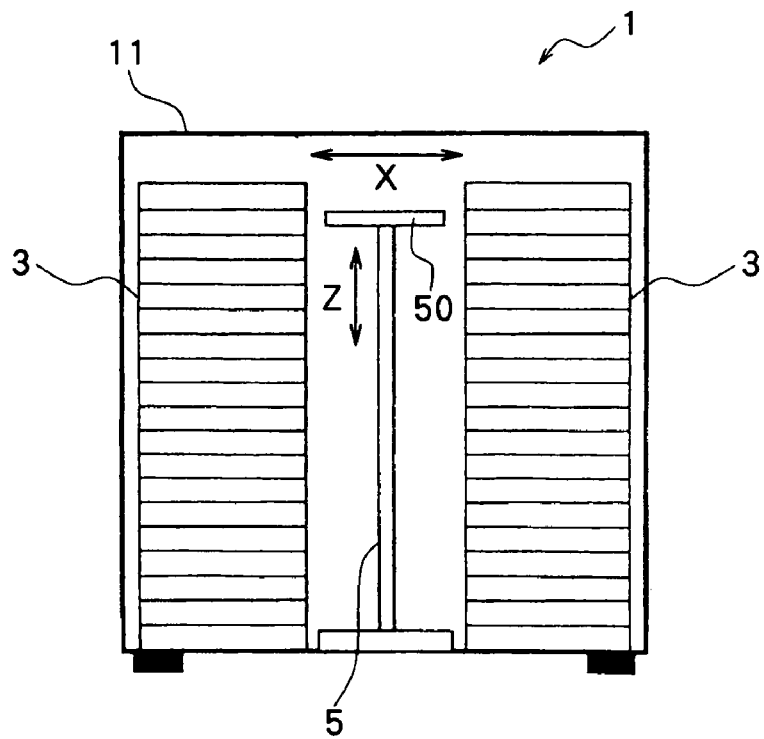
FIG. 18 is a front view showing the directions of movement of the microplate transport device in the incubator of the invention.
Figure 19:
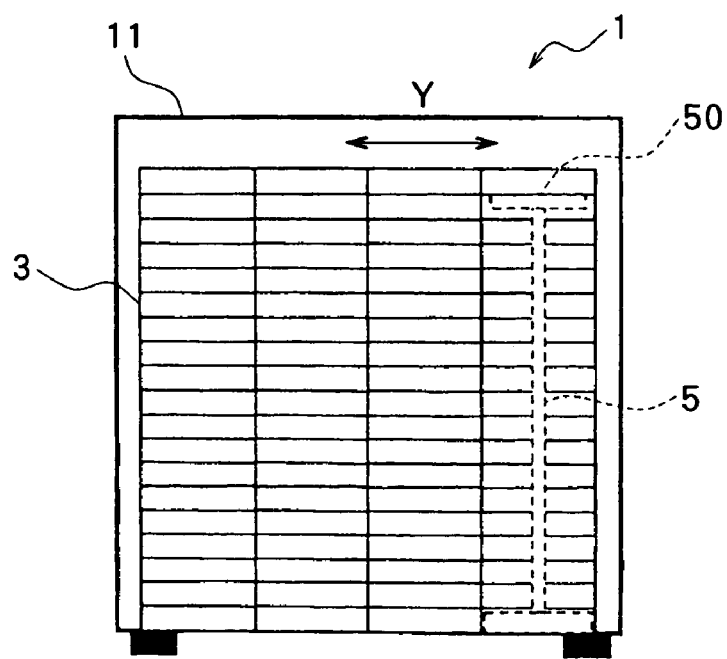
FIG. 19 is a side elevation of the same.

With the incubator 1 of the present invention, the transport table 50 is moved along the directions of X-axis, Y-axis and Z-axis by the operation of the transport device 5, with a plurality of stackers 3 installed within the chamber 11 as shown in FIGS. 18 and 19, whereby a microplate is moved into or out of the desired accommodating portion in the desired stacker 3.

For example, when a microplate 31 is to be placed into a certain microplate accommodating portion, the microplate is transported into the chamber 11 first by the microplate carriage mechanism 4. At this time, the carriage mechanism 4 is operated to cause the microplate carrier 410 to project outward from the inlet 13 of the chamber 11 as shown in FIG. 14 (see FIG. 1). After the microplate 31 is placed on the carrier 410, the carriage mechanism 4 is operated to move the carrier 410 into the chamber 11 as shown in FIG. 12.

The Y-axis transport assembly 55 and the Z-axis transport assembly 56 of the transport device 5 are operated to bring the transport table 50 to a position opposed to the microplate inlet 13, and the X-axis transport assembly 54 is moved toward the inlet 13, moving the table 50 in its reference position to a position between the carrier 410 of the carriage mechanism 4 and the microplate 31. The table 50 is then slightly raised by the operation of the Z-axis transport assembly 56 to place the microplate 31 onto the table 50, and the X-axis transport assembly 54 thereafter operates to return the table 50 to the reference position.

Subsequently, the Y-axis transport assembly 55 and the Z-axis transport assembly 56 of the device 5 are operated to move the table 50 to a position opposed to a predetermined accommodating portion of the specified stacker 3, whereupon the X-axis transport assembly 54 is operated to move the table 50 from its reference position into the accommodating portion. The Z-axis assembly 56 is then operated to slightly lower the table 50 and transfer the microplate 31 on the table 50 to the accommodating portion. This movement is followed by the operation of the X-axis assembly 54 to return the table 50 to the reference position.

When a microplate 31 in a certain microplate accommodating portion of a stacker 3 within the chamber 11 is to be brought out of the chamber 11, an operation reverse to the above placing-in and transport operation is performed. Stated more specifically, the transport table 50 is moved to a position opposed to the accommodating portion by the operation of the Y-axis and Z-axis transport assemblies 55, 56 of the transport device 5, and the X-axis transport assembly 54 is subsequently moved leftward or rightward depending on whether the accommodating portion is positioned at the left or right to move the table 50 into the accommodating portion and to position the microplate onto the table 50.

The transport device 5 then operates, transporting the microplate 31 on the table 50 to the inlet 13 of the chamber 11 and thereafter delivering the microplate 31 from the table 50 to the carrier 410 of the carriage mechanism 4. The mechanism 4 operates to move the microplate 31 on the carrier 410 out of the chamber 11.

Figure 20:
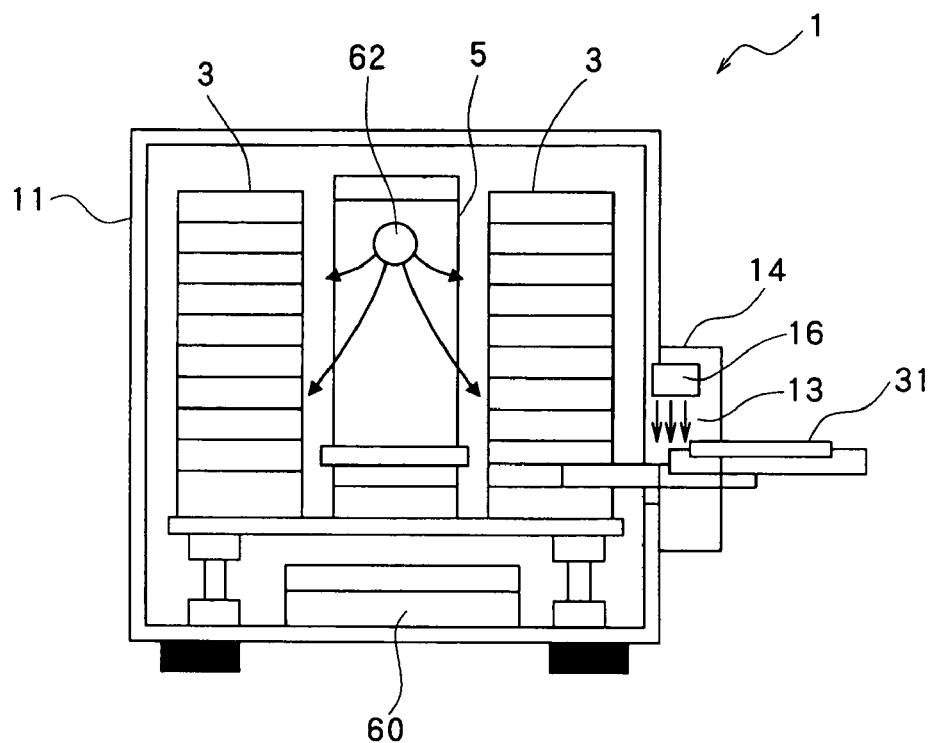
FIG. 20 is a front view for illustrating flows of a gas forced out of a discharge outlet.
Figure 21:
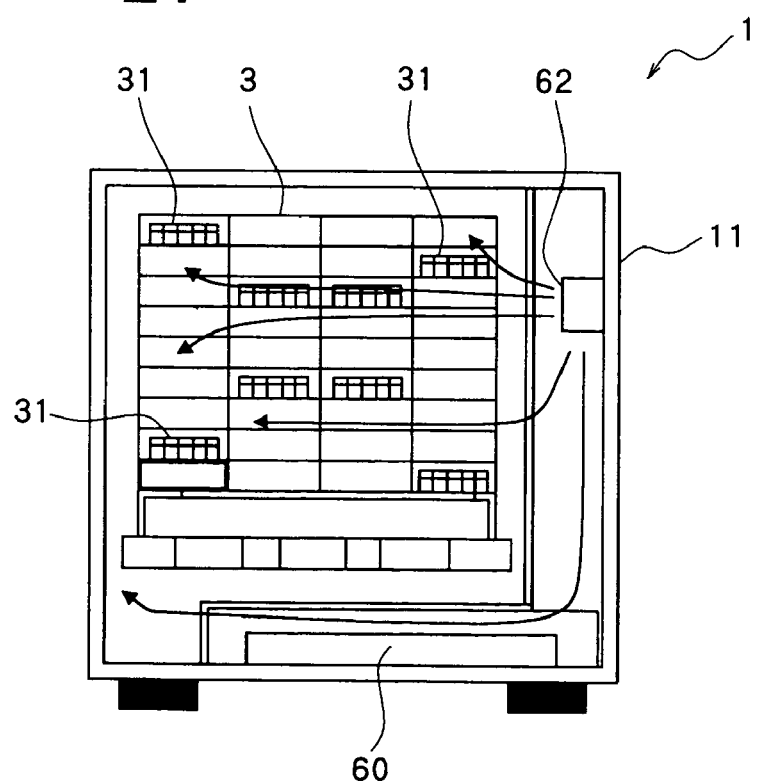
FIG. 21 is a side elevation of the same.

With reference to FIGS. 20 and 21, provided in the rear wall of the chamber 11 for a gas from the environment adjusting device 6 is the discharge outlet 62 facing toward the space wherein the transport device 5 is installed, and the stackers 3, 3 are arranged at opposite sides of the gas outlet 62. Accordingly, the gas forced out from the outlet 62 uniformly diffuses from the central portion of the chamber 11 to the surrounding area, flowing inside the chamber without producing any markedly uneven flow.

As a result, uniform ambient conditions are maintained inside the chamber 11 without any great difference produced locally, permitting the samples on the microplates 31 in the stackers 3 to be cultured under specified ambient conditions. The specified ambient conditions are maintained inside the chamber 11 because the microplate inlet 13 of the chamber 11 is opened by the shutter mechanism 14 only when microplates are brought into or out of the chamber, and also because the inlet 13 is provided with an air curtain produced by an air stream forced out from the air curtain mechanism 16.

Observation and Analysis of Sample on Microplate

Figure 22:
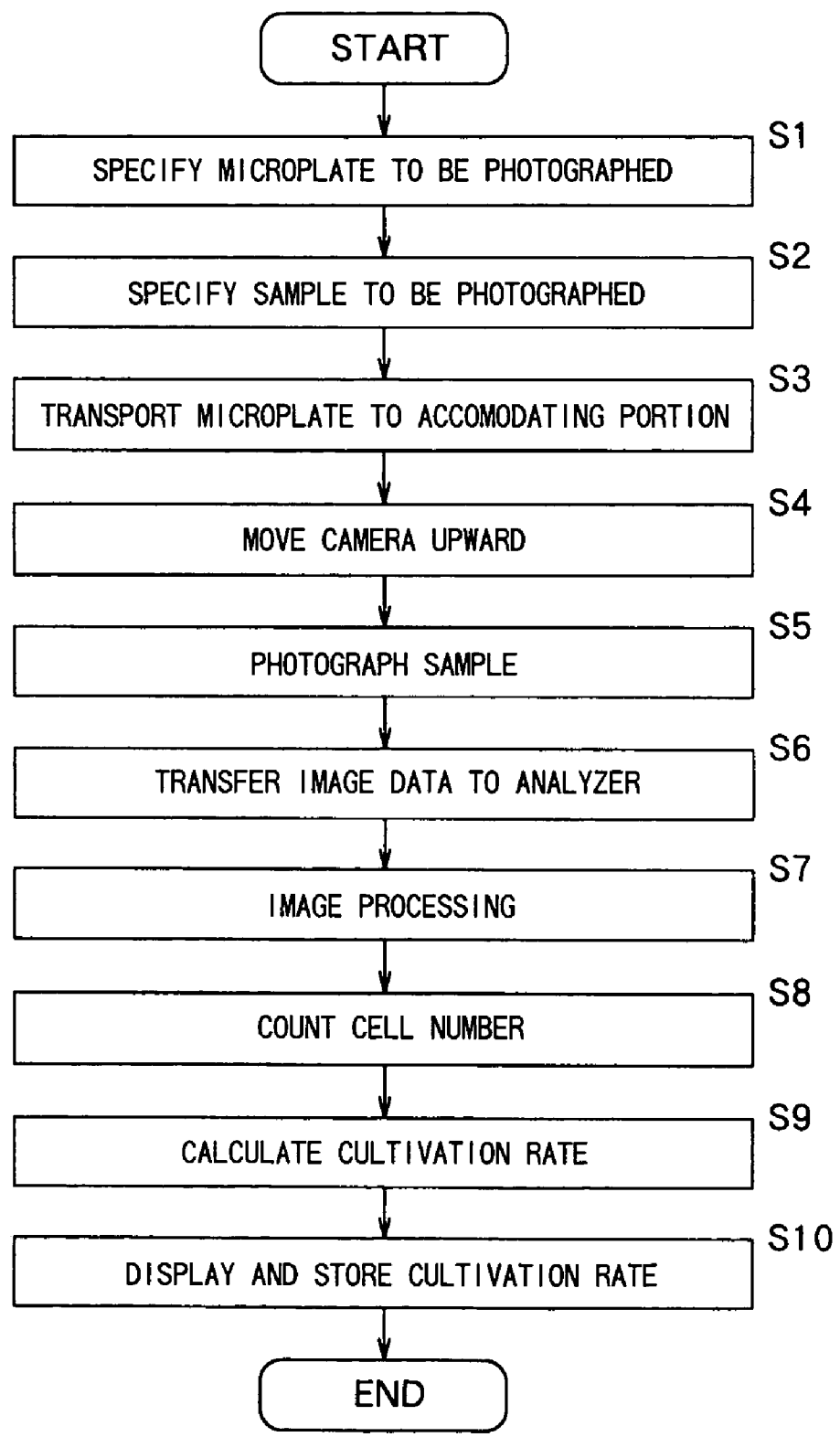
FIG. 22 is a flow chart showing a sample analysis procedure of the incubator of the invention.

The sample on the microplate 31 is observed by the camera 7 shown in FIG. 16, and the procedure shown in FIG. 22 is performed by the analyzer 72 when the growth of the sample is to be analyzed. First, the microplate 31 to be photographed is specified in step S1. The sample to be photographed on the microplate 31 is specified in step 2, whereupon the transport device 5 transports the microplate 31 to an accommodating portion wherein the microplate is to be photographed in step S3.

Figure 23:
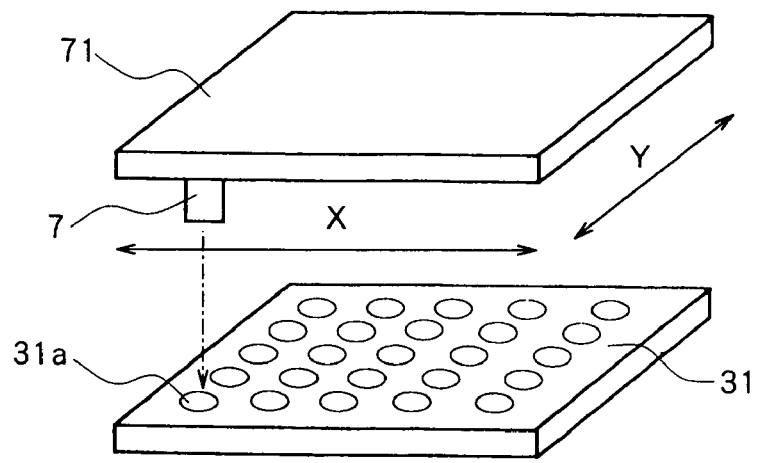
FIG. 23 is a diagram for illustrating the directions in which the camera is driven by a camera drive mechanism.

Subsequently in step S4, the camera 7 is moved in the directions of X-axis and Y-axis by the drive mechanism 71 to position the optical axis of the camera 7 on the specified sample cavity 31*a* on the microplate 31 as shown in FIG. 23. The camera 7 photographs the sample on the microplate 31 in step S5 of FIG. 22, and the image data obtained by photography is transferred to the analyzer 72 in step S6.

In the following step S7, the analyzer 72 processes the data for image processing in a predetermined manner. The number of cells in the sample is counted in step S8. In step S9, the count is compared with the number of cells before culture to calculate the culture rate. The calculated rate is shown on the display and stored in a memory.

Figure 24:
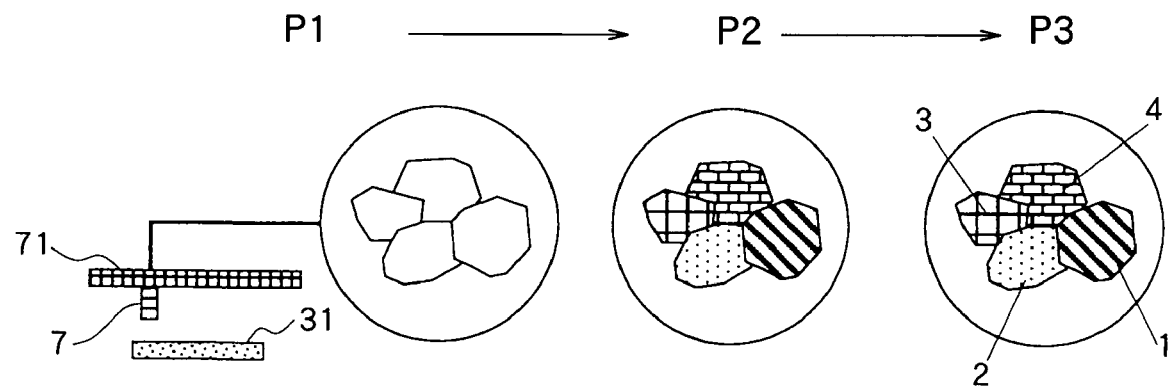
FIG. 24 is a diagram for illustrating an image processing processes.

FIG. 24 shows a sequence of processes for image processing procedure to be performed using the image data obtained from the camera 7. The contours of cells are extracted first in process P1, the cells are distinguished based on the contours in process P2, and the number of cells is counted in process P3 based on the result of distinction. Finally, the culture rate is calculated by dividing the count by the count obtained before the culture.

Another Example of Microscopic System

Figure 25:
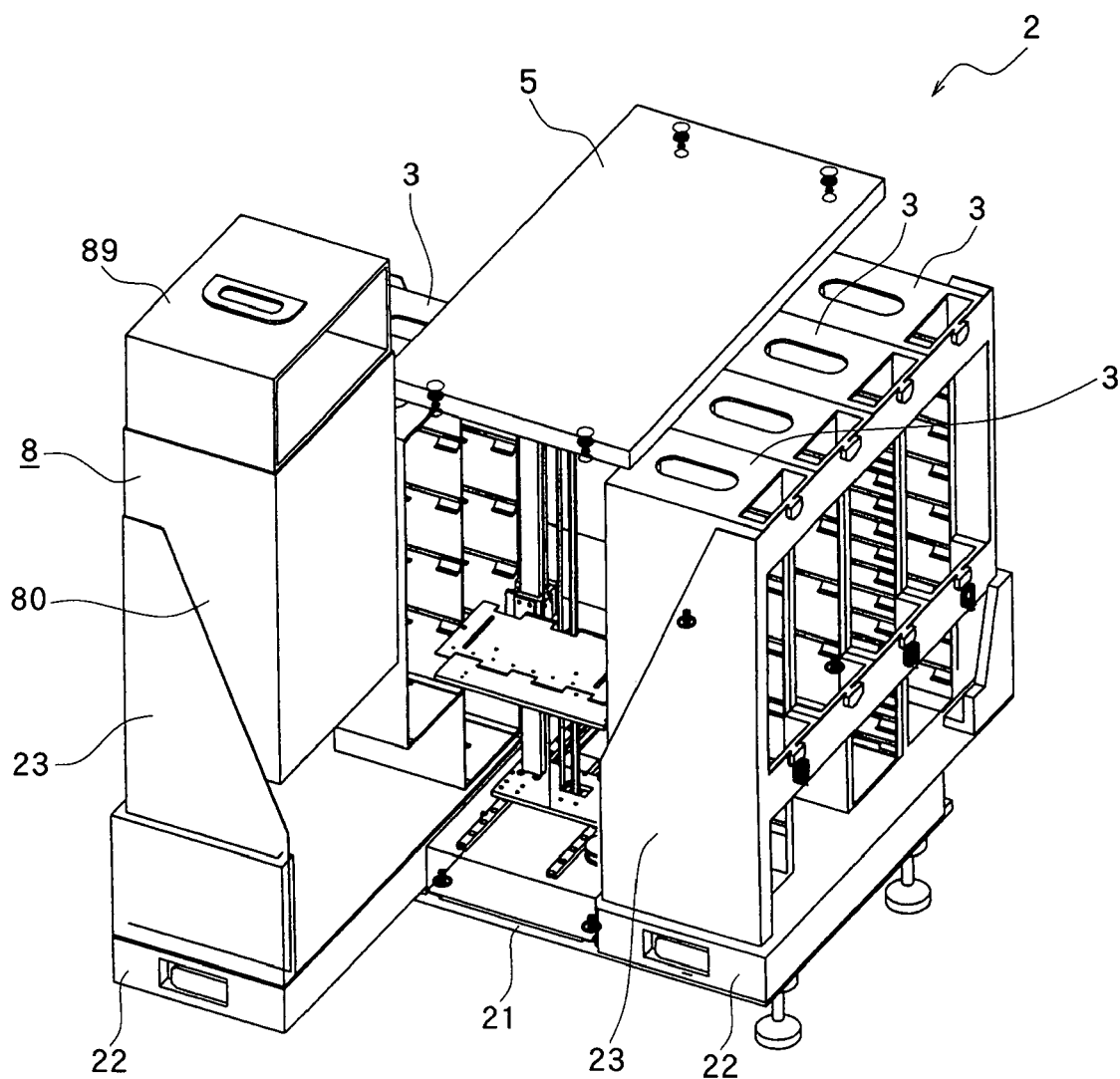
FIG. 25 is a perspective view showing the microscopic observation unit assembled into the incubator unit.

With reference to FIG. 25, the microscopic observation unit 8 can be removably attached to the stacker holder 23 in place of two stackers 3, 3 constituting the incubator unit 2.

Figure 26:
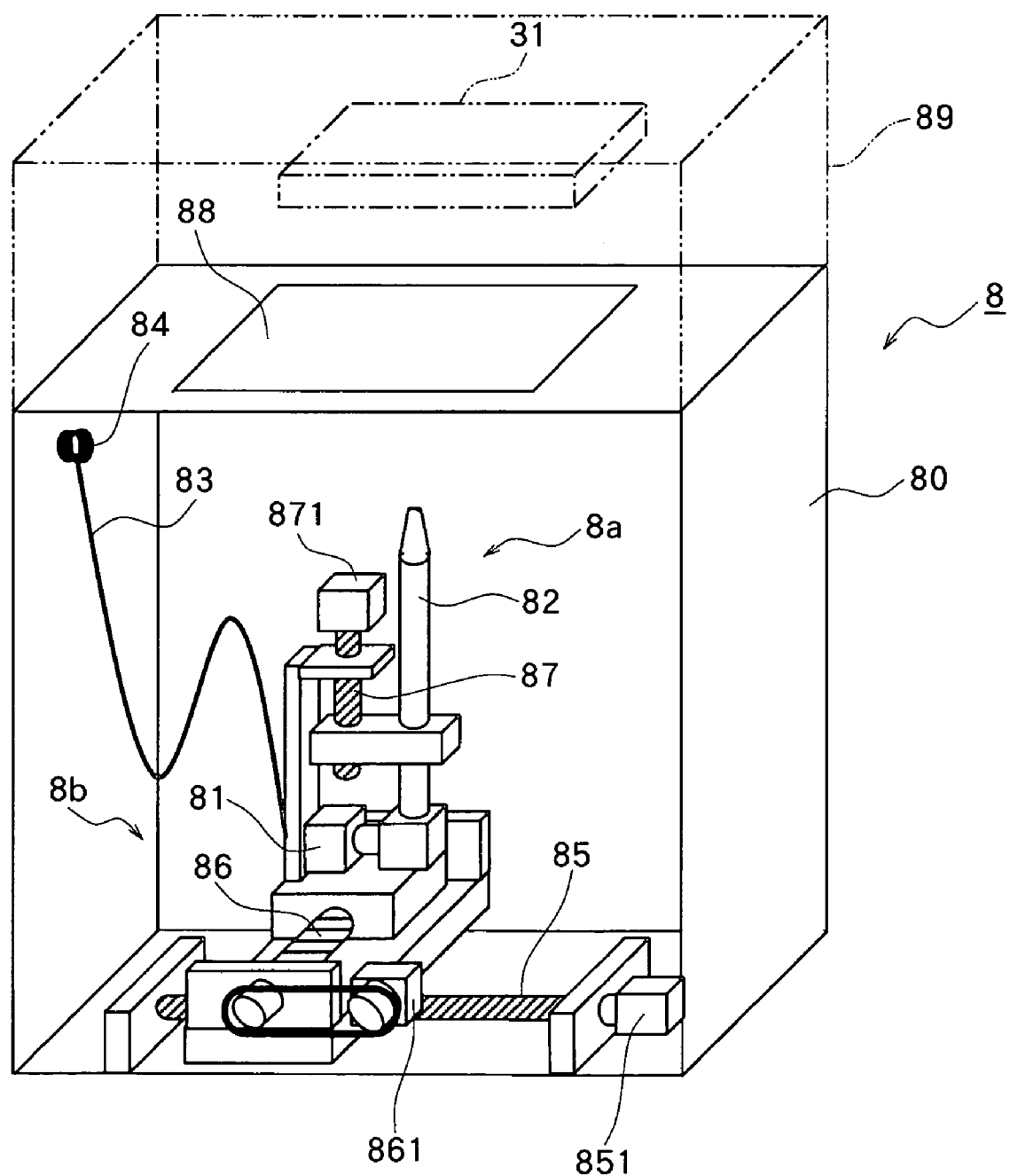
FIG. 26 is a perspective view showing the construction of the microscopic observation unit.

The microscopic observation unit 8 comprises a shield case 80 of stainless steel, and a microscopic observation device 8*a* and a drive device 8*b* disposed in the shield case 80, as shown in FIG. 26. An observation window 88 of glass plate is provided on an upper wall of the shield case 80. A microplate accommodating portion 89 is provided on an upper position of the shield case 80 for accommodating a microplate 31 in opposition to the observation window 88.

The microscopic observation device 8*a* comprises a camera 81 and an optical system 82. The optical system 82 includes a long focus lens, etc. The drive device 8*b* comprises a Y-axis drive mechanism 85 having a Y-axis motor 851, an X-axis drive mechanism 86 having an X-axis motor 861, and a Z-axis drive mechanism 87 having a Z-axis motor 871 to move the microscopic observation device 8*a* along the directions of three axes, X, Y, and Z.

Figure 27:
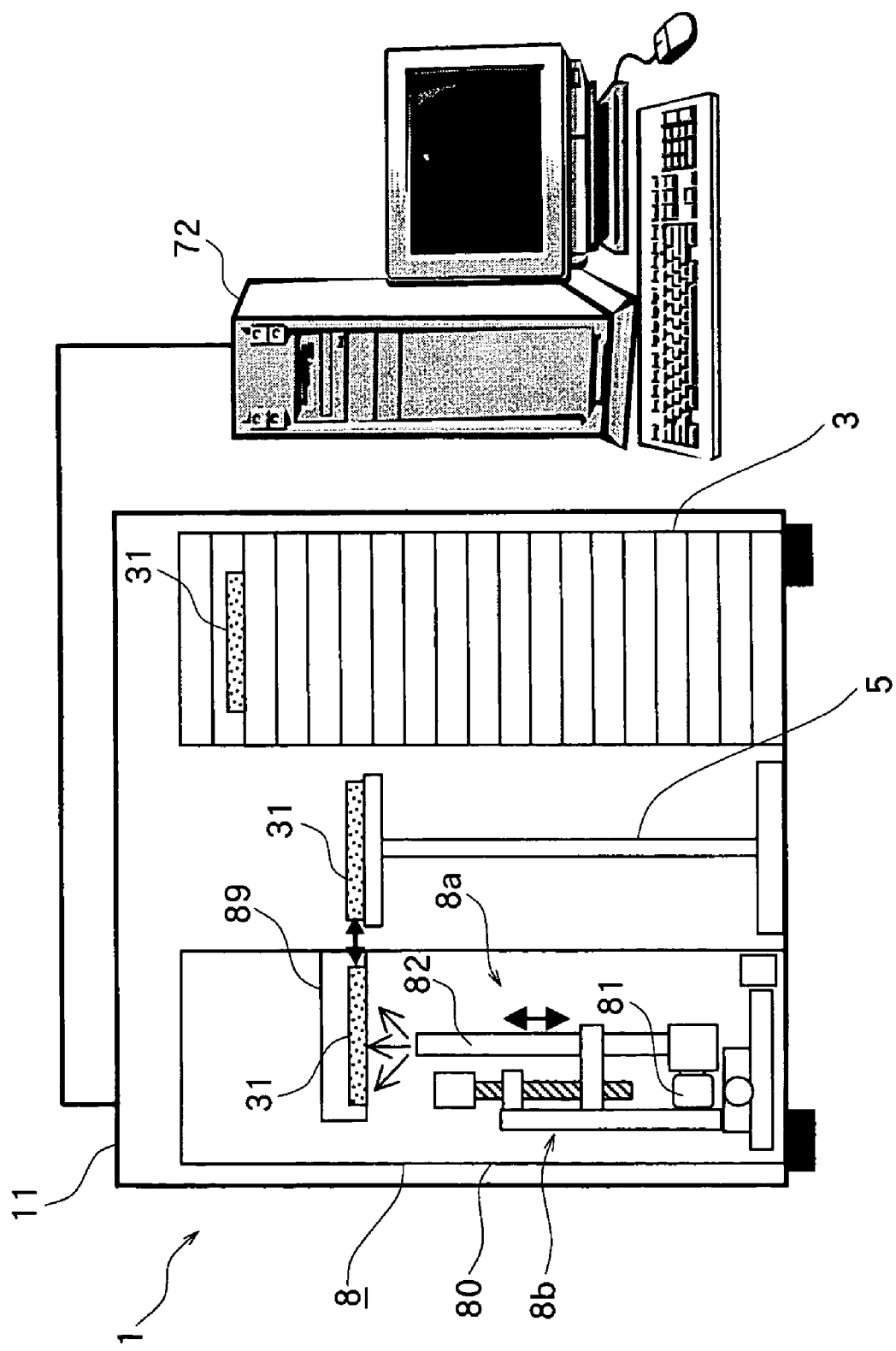
FIG. 27 is a perspective view showing the microscopic observation unit connected to an analyzer.

A signal cable 83 comprising a power line and a signal line extending from the observation device 8*a* and the drive device 8*b* is connected to a waterproof connector 84 attached to the shield case 80, and through the connector 84, to an analyzer 72 as shown in FIG. 27.

With reference to FIG. 27, when microscopic observation is to be made on the microplate 31 accommodated in the stacker 3, the micrcoplate 31 is taken out of the stacker 3 by the microplate transport device 5, is delivered to the microplate accommodating portion 89 of the microscopic observation unit 8, and is set on a predetermined position. In this state, the drive device 8*b* is moved in the direction of Z-axis to accomplish focusing. The drive device 8*b* is thereafter moved in the direction of X-axis and the direction of Y-axis to make a microscopic observation on the microplate 31. An image photographed with the camera is transmitted to the analyzer 72, which will make various analysises.

As described above, the incubator of the present invention 1 is adapted to automatically transport the microplate 31 and to accommodate a large number of microplates within the chamber 11, with the interior of the chamber held under uniform ambient conditions.

Since all motors 571, 581, 591, 421 constituting the drive mechanism of the incubator unit 2 are housed in the chamber 11 in the case of the incubator 1 of the present invention, the chamber 11 can be simpler in construction than when these motors are arranged outside the chamber 11, with the chamber 11 held highly airtight. Because the chamber 11 and the incubator unit 2 are constructed independently of each other, the microplate transport device 5 can be removed from the chamber 11 easily without being disassembled, for example, for maintenance. This ensures efficient work and makes the construction of the incubator unit 2 universally useful.

Further the incubator 1 of the present invention has a camera 7 disposed inside the chamber 11 for photographing samples on the microplate 31. This makes it possible to observe and analyze the sample without taking out the microplate 31 from the chamber 11 to the outside. This serves to hold the interior of the chamber 11 under specified ambient conditions and assure an efficient analysis.

Furthermore, with the incubator 1 shown in FIGS. 25 to 27, since the microscopic observation device 8*a* is arranged in the shield case 80 and the interior of the shield case 80 is shut out from the highly humid atmosphere of space wherein the microplate 31 is accommodated, the moisture will not cause damage to lenses etc. constituting the observation device 8*a*. Because the drive device 8*b* is housed in the shield case 80, fine dusts produced by the drive device 8*b* will not exert an adverse effect on the microplate 31.

Figure 28:
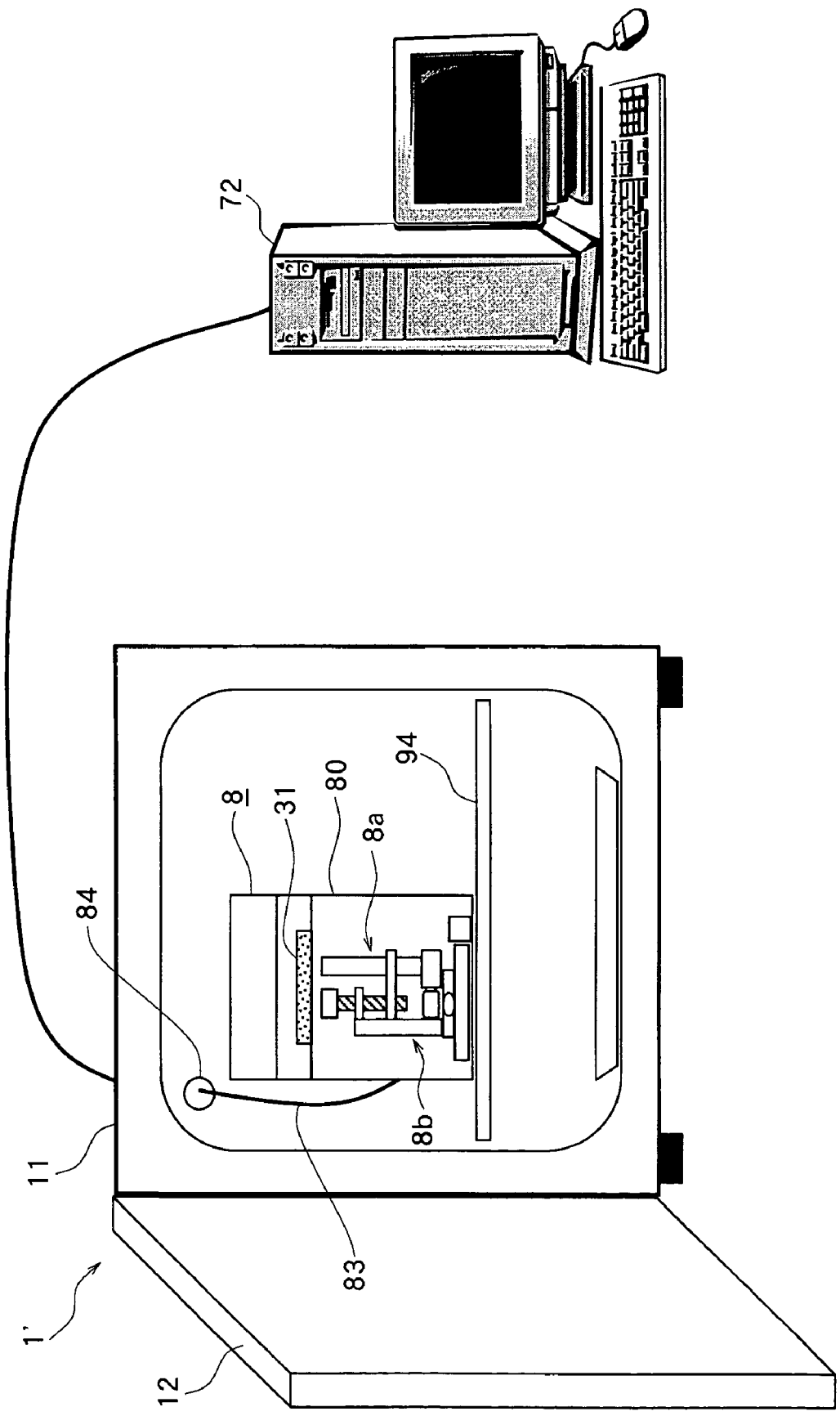
FIG. 28 is a perspective view showing an example of another incubator.
Figure 29:
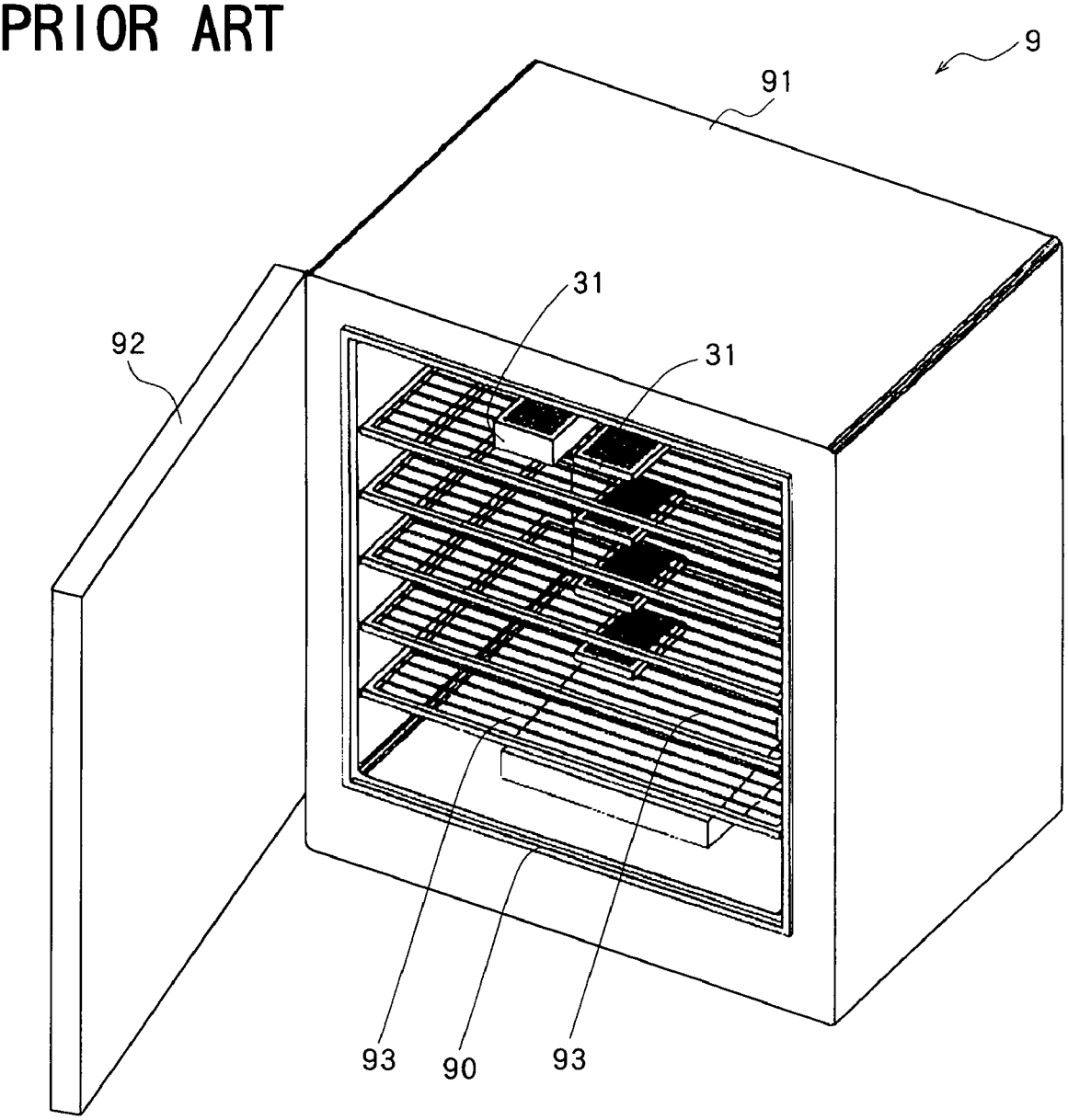
FIG. 29 is a perspective view of a conventional incubator.

The apparatus of the present invention is not limited to the foregoing embodiment in construction but can be modified variously by one skilled in the art without departing from the spirit of the invention as set forth in the appended claims. For example, as illustrated in FIG. 28, in the case of an incubator 1' which comprises a chamber 11 and a rack board 94 arranged inside the chamber 11 and does not comprise a microplate transport device, microscopic observation can be made on the microplate 31 by the provision of the microscopic observation unit 8 on the rack board 94, and the microscopic observation device 8*a* constituting the microscopic observation unit 8 can be protected from the moisture. Further usable as a culture container need not be a microplate, but can be a petri dish.

The invention claimed is:

1. An incubator comprising a chamber, the incubator being for culturing samples on culture containers inside the chamber adjusted to predetermined ambient conditions, the incubator being characterized in that a culture container accommodating rack having a plurality of culture container accommodating portions is disposed inside the chamber, a culture container transport device being adapted to move culture containers into or out of a desired culture container accommodating portions within the chamber, camera being attached in the chamber and facing a specified position wherein the culture containers are to be photographed,a control system being constructed so as to control operation of the culture container transport device, the camera, and the ambient conditions, the sample on each of the culture containers being photographable by transporting each of the culture containers to the specified position, wherein the specified position wherein each of the culture containers are to be photographed is provided on a particular accommodating portion of the accommodating rack wherein the specified position is the same position for each of the culture containers.

2. An incubator according to claim 1 wherein the camera is attached to an output end of a camera drive mechanism, and is driven into the directions of two axes along a surface of the container.

* * * * *